United States Patent [19]

Horwell et al.

[11] Patent Number: 5,244,915
[45] Date of Patent: Sep. 14, 1993

[54] AMICO ACID DERIVATIVES CYCLIZED AT THE C-TERMINAL

[75] Inventors: David C. Horwell; Martyn C. Pritchard, both of Cambridge; Reginald S. Richardson, Suffolk; Edward Roberts, Newmarket, all of England

[73] Assignee: Warner-Lambert Company, Morris Plains, N.J.

[21] Appl. No.: 726,654

[22] Filed: Jul. 12, 1991

Related U.S. Application Data

[63] Continuation-in-part of Ser. No. 576,296, Aug. 31, 1990, abandoned.

[51] Int. Cl.$^5$ ..................... A61K 31/40; C07D 209/14
[52] U.S. Cl. ..................................... 514/419; 546/87; 546/143; 546/146; 546/147; 548/495; 548/496
[58] Field of Search ............................... 548/495–496; 514/419

[56] References Cited

U.S. PATENT DOCUMENTS 4,814,463 3/1989 Kim ..................................... 548/495
4,877,785 10/1989 Hanson et al. ....................... 548/491
4,888,427 12/1989 Bodor .................................. 546/316
4,987,130 7/1991 Tsushima et al. .................... 548/491

Primary Examiner—C. Warren Ivy
Assistant Examiner—James H. Turnipseed
Attorney, Agent, or Firm—Elizabeth M. Anderson

[57] ABSTRACT

Novel α-substituted Trp dipeptoid derivatives cyclized at the C-terminal useful as agents in the treatment of obesity, hypersecretion of gastric acid in the gut, gastrin-dependent tumors, or as antipsychotics are disclosed. Further, the compounds are antianxiety agents and antiulcer agents. They are agents useful for preventing the response to the withdrawal from chronic treatment with or use of nicotine, diazepam, alcohol, cocaine, caffeine, or opioids. The compounds of the invention are also useful in treating and/or preventing panic attacks. Also disclosed are pharmaceutical compositions and methods of treatment using the compounds as well as processes for preparing them and novel intermediates useful in their preparation. An additional feature of the invention is the use of the compounds in diagnostic compositions.

12 Claims, No Drawings

AMICO ACID DERIVATIVES CYCLIZED AT THE C-TERMINAL

CROSS-REFERENCE TO RELATED APPLICATION

This application is a continuation-in-part of U.S. Ser. No. 07/576,296 filed Aug. 31, 1990 now abandoned.

BACKGROUND OF THE INVENTION

Agents acting at central cholecystokinin (CCK) receptors may induce satiety (Schick, Yaksh and Go, *Regulatory Peptides* 14:277–291, 1986). They are also expected to act as analgesics (Hill, Hughes and Pittaway, *Neuropharmacology* 26:289–300, 1987), and as anticonvulsants (MacVicar, Kerrin and Davison, *Brain Research* 406:130–135, 1987).

Reduced levels of CCK-peptides have been found in the brains of schizophrenic patients compared with controls (Roberts, Ferrier, Lee, Crow, Johnstone, Owens, Bacarese-Hamilton, McGregor, O'Shaughnessey, Polak and Bloom. *Brain Research* 288:199–211, 1983). It has been proposed that changes in the activity of CCK neurones projecting to the nucleus accumbens may play a role in schizophrenic processes by influencing dopaminergic function (Totterdell and Smith, *Neuroscience* 19:181–192, 1986). This is consistent with numerous reports that CCK peptides modulate dopaminergic function in the basal ganglia and particularly the nucleus accumbens (Weiss, Tanzer, and Ettenberg, *Pharmacology, Biochemistry and Behaviour* 30:309–317, 1988; Schneider, Allpert and Iversen, *Peptides* 4:749–753, 1983). It may therefore be expected that agents modifying CCK receptor activity may have therapeutic value in conditions associated with disturbed function of central dopaminergic function such as schizophrenia and Parkinson's disease.

CCK and gastrin peptides share a common carboxy terminal pentapeptide sequence and CCK peptides can bind to the gastrin receptor of the stomach mucosa and elicit acid secretion in many species including human (Konturek, *Gastrointestinal Hormones*, Ch. 23, pp 529–564, 1980, ed. G. B. J. Glass, Raven Press, NY). Antagonists of the CCK-B receptor would also be expected to be antagonists at the stomach gastrin receptor and this would also be of value for conditions involving excessive acid secretion.

CCK and gastrin peptides have trophic effects on the pancreas and various tissues of the gastrointestinal tract (Johnson, ibid., pp 507–527), actions which are associated with increased DNA and RNA synthesis. Moreover, gastrin secreting cells are the Zollinger-Ellison syndrome (Stadil, ibid., pp 729–739), and some colorectal tumors may also be gastrin/CCK dependent (Singh, Walker, Townsend and Thompson, *Cancer Research* 46:1612, 1986; and Smith, J. P., *Gastroenterology* 95:1541, 1988). Antagonists of CCK/gastrin receptors could therefore be of therapeutic value as antitumor agents.

The CCK peptides are widely distributed in various organs of the body including the gastrointestinal tract, endocrine glands, and the nerves of the peripheral and central nervous systems. Various biologically active forms have been identified including a 33-amino acid hormone and various carboxyl-terminus fragments of this peptide (e.g., the octapeptide CCK26-33 and the tetrapeptide CCK30-33). (G. J. Dockray, *Br. Med. Bull.* 38(3):253–258, 1982).

The various CCK peptides are thought to be involved in the control of smooth muscle contractility, exocrine and endocrine gland secretion, sensory nerve transmission, and numerous brain functions. Administration of the native peptides cause gall bladder contraction, amylase secretion, excitation of central neurons, inhibition of feeding, anticonvulsive actions and other behavioral effects. ("Cholecystokinin: Isolation, Structure and Functions," G. B. J. Glass, Ed., Raven Press, New York, 1980, pp 169–221; J. E. Morley, *Life Sciences* 27:355–368, 1980; "Cholecystokinin in the Nervous System," J. de Belleroche and G. J. Dockray, Ed., Ellis Horwood, Chichester, England, 1984, pp 110–127.)

The high concentrations of CCK peptides in many brain areas also indicate major brain functions for these peptides (G. J. Dockray, *Br. Med. Bull.* 38(3):253–258, 1982). The most abundant form of brain CCK found is CCK26 33, although small quantities of CCK30-33 exist (Rehfeld and Gotterman, *J. Neurochem.* 32:1339–1341, 1979). The role of central nervous system CCK is not known with certainty, but it has been implicated in the control of feeding (Della-Fera and Baile, *Science* 206:471–473, 1979).

Currently available appetite suppressant drugs either act peripherally, by increasing energy expenditure (such as thyroxine), or in some other manner (such as the biguanides), or act by exerting a central effect on appetite or satiety.

Centrally acting appetite suppressants either potentiate central catecholamine pathways and tend to be stimulants (for example, amphetamine), or influence serotonergic pathways (for example, fenfluramine). Other forms of drug therapy include bulking agents which act by filling the stomach, thereby inducing a "feeling" of satiety.

CCK is known to be present in some cortical interneurones which also contain gamma-aminobutyric acid (GABA) (H. Demeulemeester et al, *J Neuroscience* 8, 988–1000, 1988). Agents that modify GABA action may have utility as anxiolytic or hypnotic agents (S. C. Harvey, *The Pharmacological Basis of Therapeutics* (7th ed.) 1985, pp 339–371, MacMillan). Thus, agents which modify CCK action may have parallel anxiolytic or hypnotic activities. The role of CCK in anxiety is disclosed in TIPS 11:271–273, 1990.

SUMMARY OF THE INVENTION

The invention relates to novel compounds of the formula

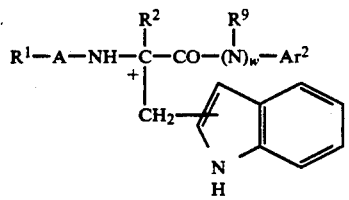

and the pharmaceutically acceptable salts thereof wherein $R^1$, $R^2$, $R^9$, A, $Ar^2$ and w are as defined hereinbelow.

In commonly assigned copending applications 07/576,308, 07/576,628, 07/576,315, 07/576,024, 07/576,297, filed on Aug. 31, 1990 by Horwell, et al, the disclosures of which are incorporated herein by reference CCK antagonists are disclosed.

In the continuation-in-part applications of the above applications also commonlY owned and copending are Ser. No. 07/726,656, filed Jul. 12, 1991, Ser. No. 07/726,655, filed Jul. 12, 1991, now abandoned. Ser. No. 07.726,653, filed Jul. 12, 1991, Ser. No. 07/726,652, filed Jul. 12, 1991, and Ser. No. 07/756,651, filed Jul. 12, 1991, by Horwell, et al, the disclosures of which are incorporated herein by reference, CCK antagonists are disclosed.

The invention also relates to a pharmaceutical composition containing an effective amount of a compound according to formula I in combination with a pharmaceutically acceptable carrier in unit dosage form effective for appetite suppression.

The compounds are also useful as anxiolytics, antipsychotics, especially for treating schizophrenic behavior, as agents in treating disorders of the extrapyramidal motor system, as agents for blocking the trophic and growth stimulating actions of CCK and gastrin, and as agents for treating gastrointestinal motility.

Compounds of the invention are also useful as analgesics and potentiate the effect of morphine. They can be used as an adjunct to morphine and other opioids in the treatment of severe pain such as cancer pain and reduce the dose of morphine in treatment of pain where morphine is contraindicated.

An additional use for compounds such as the iodinated compound is that the suitable radiolabelled iodine-131 or iodine-127 isotope gives an agent suitable for treatment of gastrin dependent tumors such as those found in colonic cancers. I-125 radiolabelled compound can also be used as a diagnostic agent by localization of gastrin and CCK B receptors in both peripheral and central tissue.

The invention further relates to a method of appetite suppression in mammals which comprises administering an amount effective to suppress appetite of the composition described above to a mammal in need of such treatment.

The invention also relates to a pharmaceutical composition for reducing gastric acid secretion containing an effective amount of a compound of formula I in combination with a pharmaceutically acceptable carrier in unit dosage form effective for reducing gastric acid secretion.

The invention also relates to a method for reducing gastric acid secretion in mammals which comprises administering an amount effective for gastric acid secretion reduction of the composition described above to a mammal in need of such treatment.

The invention also relates to a pharmaceutical composition containing an effective amount of a compound of formula I in combination with a pharmaceutically acceptable carrier in unit dosage form effective for reducing anxiety.

The invention also relates to a method for reducing anxiety in mammals which comprises administering an amount effective for anxiety reduction of the composition described above to a mammal in need of such treatment.

The invention also relates to a pharmaceutical composition containing an effective amount of a compound of formula I in combination with a pharmaceutically acceptable carrier in unit dosage form effective for treating gastrointestinal ulcers.

The invention further relates to a method for treating gastrointestinal ulcers in mammals which comprises administering an amount effective for gastrointestinal ulcer treatment of the composition as described above to a mammal in need of such treatment.

The invention also relates to a pharmaceutical composition containing an effective amount of a compound of formula I in combination with a pharmaceutically acceptable carrier in unit dosage form effective for treating psychosis, i.e., schizophrenia.

The invention further relates to a method for treating psychosis in mammals which comprises administering an amount effective for treating psychoses of a composition as described above to a mammal in need of such treatment.

The invention also relates to pharmaceutical compositions effective for stimulating or blocking CCK or gastrin receptors, for altering the activity of brain neurons, for schizophrenia, for treating disorders of the extrapyramidal motor system, for blocking the trophic and growth stimulating actions of CCK and gastrin, and for treating gastrointestinal motility.

The invention also relates to a pharmaceutical composition for preventing the withdrawal response produced by chronic treatment or abuse of drugs or alcohol.

The invention further relates to a method for treating the withdrawal response produced by withdrawal from chronic treatment or withdrawal from abuse of drugs or alcohol. Such drugs include benzodiazepines, especially diazepam, cocaine, alcohol, and nicotine. Withdrawal symptoms are treated by administration of an effective withdrawal treating amount of a compound of the instant invention.

The invention also relates to a pharmaceutical composition containing an effective amount of a compound of formula I in combination with a pharmaceutically acceptable carrier in unit dosage form effective for treating and/or preventing panic.

The invention also relates to a method for treating and/or preventing panic in mammals which comprises administering an amount effective for panic treatment and/or prevention of the composition described above to a mammal in need of such treatment.

The invention further relates to the use of the compounds of formula I to prepare pharmaceutical and diagnostic compositions for the treatment and diagnosis of the conditions described above.

The invention further provides processes for the preparation of compounds of formula I.

The invention further provides novel intermediates useful in the preparation of compounds of formula I and also provides processes for the preparation of the intermediates.

DETAILE DESCRIPTION

The compounds of the present invention are derivatives of α-methyl tryptophan differing from natural dipeptides in that the substituent group $R^2$ is not hydrogen.

The compounds of the present invention are represented by the formula

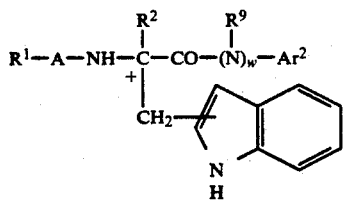

or a pharmaceutically acceptable salt thereof wherein:

$R^1$ is a cyclo or polycycloalkyl hydrocarbon of from three to twelve carbon atoms with from zero to four substituents, each independently selected from the group consisting of: a straight or branched alkyl of from one to six carbon atoms, halogen, CN, OR*, SR*, $CO_2R^*$, $CF_3$, $NR^5R^6$, or $-(CH_2)_nOR^5$, wherein R* is hydrogen, straight or branched alkyl of from one to six carbon atoms, $R^5$ and $R^6$ are each independently hydrogen or alkyl of from one to six carbon atoms; and n is an integer from zero to six;

A is $-(CH_2)_nCO-$, $-SO_2-$, $-SO-$, $-NHCO-$,

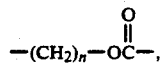

$-SCO-$, $-O-(CH_2)_nCO-$ or $-HC=CHCO-$ wherein n is an integer from zero to six;

$R^2$ is a straight or branched alkyl of from one to six carbon atoms, $=HC=CH_2$, $-C\equiv CH$, $-(CH_2)_n-CH=CH_2$, $-(CH_2)_nC\equiv CH$, $-(CH_2)_nAr$, $-(CH_2)_nOR^*$, $-(CH_2)_nOAr$, $-(CH_2)_nCO_2R^*$, $-(CH_2)_nNR^5R^6$ wherein n, R, $R^5$, and $R^6$ are as defined above and Ar is a mono or polycyclic unsubstituted or substituted carbo- or heterocyclic aromatic or hydroaromatic moiety;

$R^9$ is H, or a straight or branched alkyl of from one to six carbon atoms, $-(CH_2)_nCO_2R^*$, $(CH_2)_nOAr'$, $(CH_2)_nAr'$, $(CH_2)_nNR^5R^6$, wherein n, R*, $R^5$, and $R^6$ are as defined above or taken from $R^3$ and Ar, independently taken from Ar and w is zero or 1;

Ar2 is

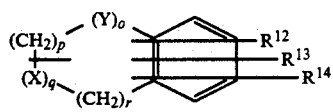

wherein x and y are each independently O, S, N, $CH_2$, $-CHR^{12}$, $-NR^{12}-$, $-NR^{12}CO$, $C=N-$, $-C=C-$, or $-C(=O)$ or a bond; o, p, q, and r are each independently an integer of from 0 to 3, provided that when o, p, q, and r are all simultaneously zero, Ar2 becomes

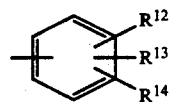

$R^{12}$, $R^{13}$, and $R^{14}$ are each independently halogen, $R^2$ as is defined above, $-(CH_2)_g-B-D$ wherein g is an integer of from 0 to 6 wherein B is a bond,
 $-OCO(CH_2)_n-$,
 $-O(CH_2)_n-$,
 $-NHCO(CH_2)_n-$,
 $-CONH(CH_2)_n-$,
 $-NHCOCH=CH-$,
 $-COO(CH_2)_n-$,
 $-CO(CH_2)_n-$,
 $-S(CH_2)_n-$,
 $-SO(CH_2)_n-$,
 $-SO_2(CH_2)_n-$,

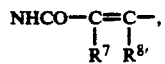

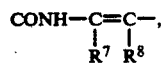

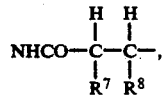

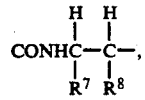

$-NHSO_2-(CH_2)_n-$, or
$-SO_2NH-(CH_2)_n-$ wherein $R^7$ and $R^8$ are independently selected from hydrogen and $R^2$, or together form a ring $(CH_2)_m$ wherein m is an integer of from 1 to 5 and n is as defined above;

D is
 $-COOR^*$,
 $-CH_2OR^*$,
 $-CHR^2OR^*$,
 $-CH^2SR^*$,
 $-CHR^2SR^*$,
 $-CONR^5R^6$,
 $-CN$,
 $-NR^5R^6$,
 $-OH$,
 $-H$, and acid replacements such as tetrazole,

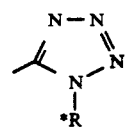

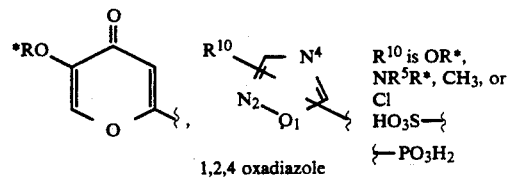

1,2,4 oxadiazole

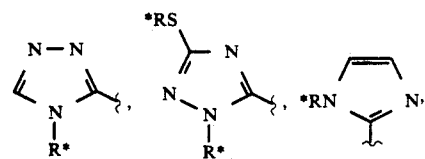

-continued $R^{11}$ is CN, $CO_2H$, or $CF_3$,

PhSO$_2$NHCO—,
CF$_3$CONHCO—,
CF$_3$SO$_2$NHCO—,
H$_2$NSO$_2$—, wherein s is an integer of from 0 to 2
wherein R*, $R^2$, $R^5$, and $R^6$ are as defined above.

Other preferred compounds of the instant invention are those wherein
$R^1$ is wherein W, X, Y, and Z are each independently hydrogen, a straight or branched alkyl of from one to six carbon atoms, $CF_3$, $NR^5R^6$, —(CH$_2$)$_n$CO$_2$R*, or CN, F, Cl, Br, OR*, SR*, wherein R* is hydrogen or a straight or branched alkyl of from one to six carbon atoms and $R^5$ and $R^6$ are as defined above and n is an integer of 1 to 3.

A is
—NHCO—,
—OCO—,
—SO$_2$—,
—S(=O)—,
—CH$_2$CO—, $R^2$ is
—CH$_3$,
—CH$_2$CO$_2$CH$_3$,
—CH$_2$C≡CH, $R^9$ is hydrogen,
when w is 1, Ar$^2$ is unsubstituted or substituted in the manner indicated above such as and when w is zero, Ar$^2$ is unsubstituted or substituted in the manner indicated above such as -continued

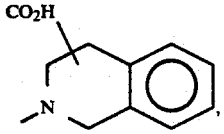

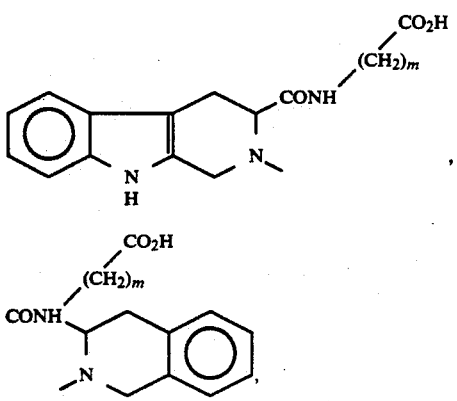

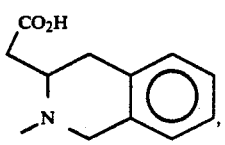

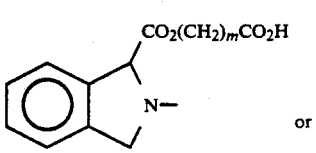

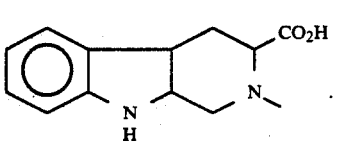

or

More preferred compounds of the instant invention are those wherein $R^1$ is 2-adamantyl or 1-(S)-endobornyl,
A is $$-O-\overset{O}{\underset{\|}{C}}-,$$

$R^2$ is —CH$_3$, X and Y are —CH$_2$— when p, q, and r are 1; and

Ar$^2$ is unsubstituted, or may be substituted by one to three substituents each independently selected from —CH$_2$OH, —CH$_2$OCOCH$_2$CH$_2$COOH, —CH$_2$OCOCH=CHCO$_2$H, —CH$_2$NHCOCH$_2$CH$_2$COOH, —CH$_2$NHCOCH=CHCOzH, -NHCOCH=CHCOzH, —NHCOCH$_2$CH$_2$CO$_2$H, hydroxy, phenyl, CO$_2$Me, benzyl, CONHCH$_2$CH$_2$CO$_2$Bz, —CO$_2$Bz, CH$_2$SCH$_2$CO$_2$H, —CONHCH$_2$CO$_2$H, —CONHCH$_2$CH$_2$CO$_2$H, or —CH$_2$SCH$_2$CO$_2$H.

Small x and small y can be independently carbonyl.

The D and the L configurations are possible at the chiral centers and are included in the scope of the invention:

Preferred is when $R^2$ is —CH$_3$[D] configuration.
Preferred compounds of the instant invention are:

[2-[(2,2-Diphenylethyl)amino] 1-(1H-indol-3-ylmethyl)-1-methyl-2-oxoethyl]carbamic acid, tricyclo[3.3.1.1$^{3,7}$]dec-2-yl ester,

[2-[(3,4-dihydro-2H-1-benzopyran-3-yl)amino]-1-(1H-indol 3-ylmethyl)-1-methyl -2-oxoethyl]carbamic acid, tricyclo[3.3.1.1$^{3,7}$]dec 2-yl ester,

[2-[(1H inden-1-ylmethyl)amino]-1-(1H-indol-3-ylmethyl)-1-methyl-2-oxoethyl]carbamic acid, tricyclo[3.3.1.1$^{3,7}$]dec-2-yl ester,

[2-[[(2,3-dihydro-1-hydroxy-1-H-inden-1-yl)methyl]amino]-1-(1H-indol-3-ylmethyl) -1-methyl-2-oxoethyl]carbamic acid, tricyclo[3.3.1.1$^{3,7}$]dec-2-yl ester,

[1-(1H-indol-3-ylmethyl)-1-methyl-2-oxo-2-[(1,2,3,4-tetrahydro-2-naphthalenyl) amino]ethyl]carbamic acid, tricyclo[3.3.1.13,7]dec-2-yl ester,

[2-[(1,2-diphenylethyl)amino]-1-(1H-indol-3-ylmethyl)-1-methyl-2-oxoethyl]carbamic acid, tricyclo[3.3.1.1$^{3,7}$]dec-2-yl ester,

[1-(1H-indol-3-ylmethyl)-1-methyl-2-oxo-2-[[(1-phenyl-1-cyclopentyl)methyl]amino]ethyl]carbamic acid, tricyclo[3.3.1.1$^{3,7}$]dec-2-yl ester,

[2-(dipentylamino)-1-(1H-indol-3-ylmethyl)-1-methyl-2-oxoethyl]carbamic acid, tricyclo-[3.3.1.1$^{3,7}$]dec-2-yl ester,

[2-(3-azabicyclo[3.2.2]non-3-yl)-1-(1H-indol-3-ylmethyl)-1-methyl-2-oxoethyl]carbamic acid, tricyclo[3.3.1.1$^{3,7}$]dec-2-yl ester,

[1-(1H-indol-3-ylmethyl)-2-(octahydro-1H-indol-1-yl)-1-methyl-2-oxoethyl]carbamic acid, tricyclo[3.3.1.1$^{3,7}$]dec-2-yl ester,

[2-(decahydro-2-isoquinolinyl)-1-(1H-indol-3-ylmethyl)-1-methyl-2-oxoethyl]carbamic acid, tricyclo[3.3.1.1$^{3,7}$]dec-2-yl ester,

[2-[bis(phenylmethyl)amino]-1-(1H-indol-3-ylmethyl)-1-methyl-2-oxoethyl]carbamic acid, tricyclo[3.3.1.1$^{3,7}$]dec-2-yl ester,

[2-(3-azaspiro[5.5]undec-3-yl)-1-(1H-indol-3-ylmethyl)-1-methyl-2-oxoethyl]carbamic acid, tricyclo[3.3.1.1$^{3,7}$]dec 2-yl ester,

[1-(1H indol-3-ylmethyl)-1-methyl-2-oxo-2-(2,3,4,9-tetrahydro-1H-pyrido[3,4-b]indol-2-yl)ethyl]carbamic acid, tricyclo[3.3.1.1$^{3,7}$]dec-2-yl ester,

[1-(1H-indol-3-ylmethyl)-1-methyl-2-oxo-2-(1,3,3-trimethyl-6-azabicyclo[3.2.1]oct-6-yl)ethyl]carbamic acid, tricyclo[3.3.1.1$^{3,7}$]dec-2-yl ester.

Most preferred compounds of the instant invention are:

1. Carbamic acid, [2-[(2,3-dihydro-2-hydroxy-1H-inden-1-yl)amino]-1-(1H-indol-3-ylmethyl)-1-methyl-2-oxoethyl]-, 1,7,7-trimethylbicyclo-[2.2.1]hept 2-yl ester (bicyclo ring is 1S-endo (+-isomer), trp center is D, indene ring centers are unknown), 2. Carbamic acid, [2-[(2,3-dihydro-1-hydroxy-1H-inden-2-yl)amino]-1-1H-indol-3-ylmethyl)-2-methyl-2-oxoethyl]-, 1,7,7-trimethylbicyclo-[2.2.1]hept-2-yl ester, [1S*[1α,2β[S-(trans)],4α]]- (Bicyclo system is 1S-endo), 3. Carbamic acid, [2-[(2,3-dihydro 1-hydroxy-1H-inden-2-yl)amino]-1-(1H-indol-3-ylmethyl)-1-methyl-2-oxoethyl]-, 1,7,7-trimethylbicyclo-[2.2.1]hept-2-yl ester, [1S-[1α,2β [S*(1S*.2S*)],4α]]- [Bicyclo system is 1S-endo, all other centers are R], 4. Carbamic acid, [1-(1H-indol-3-ylmethyl)-1 methyl-2-oxo-2-[(1,2,3,4-tetrahydro-1-oxo 2-naphthalenyl)amino]ethyl]-, 1,7,7-trimethyl-bicyclo[2.2.1]hept-2-yl ester (Bicyclo system 1S-endo; TRP center R; naphthyl center (−) or (+)), (Isomer II), 5. Carbamic acid, [1-(1H-indol-3 ylmethyl)-1-methyl-2-oxo-2-[(1-2,3,4-tetrahydro-1-oxo-2-naphthalenyl-)amino]ethyl]-, 1,7,7-trimethylbicyclo[2.2.1.1]hept-2-yl ester (Bicyclo system 1S-endo; TRP center R; naphthyl center (+) or (-)), (Isomer I), 6. Carbamic acid, [1-(1H-indol-3-ylmethyl)-1-methyl-2-oxo-2-[(1,2,3,4-tetrahydro-1-naphthalenyl)amino]ethyl]-, tricyclo[3.3.1.1$^{3,7}$]-dec-2-yl ester, (±)-, 7. Carbamic acid, [1-1H-indol-3-ylmethyl)-1-methyl-2-oxo-2 [(1,2,3,4-tetrahydro -2-naphthalenyl)amino]ethyl]-, tricyclo[3.3.1.1$^{3,7}$]-dec-2-yl ester, (±)-, 8. Carbamic acid, [1-(1H-indol-3-ylmethyl)-1-methyl-2-oxo-2-(1,2,3,4-tetrahydro-2-isoquinolinyl)ethyl]-, tricyclo[3.3.1.1$^{3,7}$]-dec-2-yl ester, (R)-, 9. 4-[4-[3-(1H-indol-3-yl)-2-methyl-1-oxo-2-[[(1,7,7-trimethylbicyclo[2.2.1]hept-2-4-oxobutanoic acid (Isomer II) (Bicyclo system is 1S-endo, phenyl center is S or R, other center is R), 10. 4-[4-[3-(1H-indol-3-yl)-2-methyl-1-oxo 2-[[[(1,7,7-trimethylbicyclo[2.2.1]hept-2-yl)oxy]-carbonyl-]amino]propyl]-2-phenyl-1-piperazinyl]-4-oxobutanoic acid (Isomer I) (Bicyclo system is 1S-endo, phenyl center is R or S, other center is R), 11. 1,7,7-trimethylbicyclo[2.2.1]hept-2-ylmethyl)-1-methyl-2-oxo-2-(3-phenyl-1-piperazinyl)ethyl]carbamate (Bicyclo system is 1S-endo, phenyl is RS, other is R), 12. [1S-[1α,2β(S*),4α]]-4-[[[1-[3-(1H-indol-3-yl) -2-methyl-1-oxo-2-[[[(1,7,7-trimethylbicyclo-[2.2.1]hept-2-yl)oxy]carbonyl]amino]propyl]-4-phenyl-4-piperidinyl]methyl]amino]-4-oxobutanoic acid (Bicyclo system is 1S endo), 13. 1,7,7-trimethylbicyclo[2.2.1]hept-2-yl[1S-[1α,2β(S*),4α]]-[2-(4-hydroxy-4-phenyl-1-piperidinyl) -1-(1H-indol-3-ylmethyl)-1-methyl-2-oxoethyl]-carbamate (Bicyclo system is 1S-endo, TRP is R), 14. [1S-(1α,2β,4α)]-N-[N-[α-methyl N-[[(1,7,7-trimethylbicyclo[2.2.1]hept-2-yl)oxy]carbonyl]-D-trytophyl]-L-prolyl]-β-alanine (Bicyclo system is 1S-endo), 15. Phenylmethyl[1S-(1α,2β,4α)]-1-[α-methyl-N-[[(1,7,7-trimethylbicyclo[2.2.1]hept-2-yl)-oxy]carbonyl]-D-tryptophyl]-L-proline (Bicyclo system is 1S-endo), 16. [1S-[1α,2β(S*,R*),4α]]-[1-[3-(1H-indol-3-yl)-2-methyl -1-oxo-2-]]](1,7,7-trimethylbicyclo[2.2.1]hept-2-yl)oxy]carbonyl]amino]propyl]-3-pyrrolidinyl]-methyl butanedioate, 17. Mono 1-[3-[(1H-indol-3-yl)-2-methyl-1-oxo-2-[[[(1,7,7-trimethylbicyclo[2.2.1]hept-2-yl)oxy]carbonyl]amino]propyl]-3-pyrrilidinyl-butanedioate (Bicyclo system is 1S-endo, pyrrolidine center is RS, other center is R), 18. 1,7,7-trimethylbicyclo[2.2.1]hept-2-yl[2-(3-hydroxy-1-pyrrolidinyl) -1-(1H indol-3-ylmethyl)-1-methyl-2-oxoethyl]carbamate (ring is 1S-endo, hydroxy center is RS, other center is R), 19. Phenylmethyl (1S-endo)N-[1-[α-methyl-N-[[(1,7,7-trimethylbicyclo[2.2.1]hept-2-yl)oxy]carbonyl]-D-trytophyl]-L-prolyl]-β-alanine, 20. Methyl-N-[α-methyl-N-[[(1,7,7-trimethylbicyclo-[2.2.1]hept-2-yl)oxy]carbonyl]-D-tryptophyl]-L-proline (mixture of 1S-exo and 1S endo isomers), 21. N-[α-methyl-[[(1,7,7 trimethylbicyclo[2.2.1]-hept-2-yl)oxy]carbonyl]-D-trytophyl]-L-proline (mixture of 1S-exo and 1S endo isomers), 22. Tricyclo[3.3.1.1$^{3,7}$]dec-2-yl(±)-[1-(1H-indol-3-ylmethyl) -1-methyl-2-oxo-2-[(1,2,3,4-tetrahydro-2-naphthalenyl)amino]ethyl]carbamate, 23. Tricyclo[3.3.1.1$^{3,7}$]dec-2-yl(±)-[1-(1H-indol-3-ylmethyl) -1-methyl-2-oxo-2-[(1,2,3,4-tetrahydro-1-naphthalenyl)amino]ethyl]carbamate, 24. 2,2,2-trifluoro 1-phenylethyl[2-[[1-(hydroxymethyl)-2-phenylethyl]amino]-1-(1H-indol 3-ylmethyl)-1-methyl-2-oxoethylcarbamate (Isomer II) (tryptophan center L or D hydroxy center S trifluoromethyl center R), 25. (R)-N-[1-[(methylphenylamino)carbonyl]-3-phenylpropyl]-1H-Indole-4-acetamide, 26. 2-[[[(3-methylphenyl)amino]carbonyl]amino]-N-[2-(phenylmethyl)phenyl]acetamide, 27. [1S-[1α,2β(S*),4α]]-1,7,7-trimethylbicyclo[2.2.1]-hept-2-yl-[2-(3,4-dihydro-2(1H)-isoquinolinyl) -1-(1H-indol-3-ylmethyl)-1-methyl-2-oxoethyl]carbamate (Bicyclo system is 1S-endo), 28. Tricyclo[3.3.1.1$^{3,7}$]dec-2-yl (±)-[2-[(2,3-dihydro-1-H-inden-2-yl)amino]-1-(1H-indol-3-ylmethyl)-1-methyl-2-oxoethyl]carbamate, 29. Tricyclo[3.3.1.1$^{3,7}$]dec-2-yl(±)-[2-[(2,3-dihydro-1H-inden-1-yl)amino]1-(1H-indol-3-ylmethyl)-1-methyl-2-oxoethyl]carbamate, 30. Tricyclo[3.3.1.1$^{3,7}$]dec-2-yl-(R)-[1-(1H-indol-3-ylmethyl)-1-methyl-2-oxo-2-(1,2,3,4 tetrahydro-2-isoquinolinyl)ethyl]carbamate, 31. 4-[[1,2,3,4-Tetrahydro-2-[[3-(1H-indol-3-yl)-2-methyl-1-oxo-2-[[(tricyclo[3.3.1.1$^{3,7}$]dec-2-yloxy)-carbonyl]amino]propyl]amino]-1-naphthalenyl]amino]-4-oxobutanoate, 32. Tricyclo[3.3.1.1$^{3,7}$]dec-2-yl-[2-[(1-azido-1,2,3,4-tetrahydro-2-naphthalenyl)amino -1(1H-indol-3-ylmethyl)-1-methyl-2-oxoethyl]carbamate, 33. Methyl 3-[[2-[[3-(1H-indol-3-yl)-2-methyl-1-oxo-2-[[(tricyclo[3.3.1.1$^{3,7}$]dec-2-yloxy)carbonyl]amino]-propyl]amino]-1,2,3,4-tetrahydro-1-naphthalenyl]-amino]-3-oxopropanoate, 34. Methyl 3-[[2-[[3-(1H-indol-3-yl)-2-methyl-1-oxo-2-[[(tricyclo[3.3.1.1$^{3,7}$]dec-2-yloxy)carbonyl]amino]-propyl]amino]-1,2,3,4-tetrahydro-1-naphthalenyl-]amino]-3-oxopropanoate, and 35. Methyl 1-[[1,2,3,4-tetrahydro-2-[[3-(1H-indol-3-yl)-2-methyl-1-oxo -2-[[(tricyclo[3.3.1.1$^{3,7}$]dec-2-yloxy)-carbonyl]amino]propyl]amino]-1-naphthalenyl]-amino]-4-oxo-2-butanoate.

Table I below illustrates representative compounds of the invention. Stereochemistry is not shown in the Table I in all instances. The numbers in the first column refer to the numbered compounds on the previous pages.

TABLE I $$R^1-A-NH-\overset{R^2}{\underset{CH_2-\text{(indole)}}{\overset{+}{C}}}-CO-(N)_w-Ar^2$$
$$\phantom{R^1-A-NH-C-CO-(N)_w}R^9$$

| Example Number | R¹ | A | R² | R⁹ | w | Ar² |
|---|---|---|---|---|---|---|
| 1 | 2-adamantyl | O—CO | Me | Null | 0 | 2-methyl-N-methyl-tetrahydroisoquinoline |
| 2 | (S-endo) 1,7,7-trimethylnorbornyl | O—CO | Me (R) | H | 1 | 2-methyl-tetralone (Isomer I) |
| 3 | (S-endo) 1,7,7-trimethylnorbornyl | O—CO | Me (R) | H | 1 | 2-methyl-tetralone (Isomer II) |
| 4 | (S-endo) 1,7,7-trimethylnorbornyl | O—CO | Me (R) | H | 1 | (1R,2R)-2-hydroxy-indanyl |
| 5 | (S-endo) 1,7,7-trimethylnorbornyl | O—CO | Me (R) | H | 1 | (1S,2S)-2-hydroxy-indanyl |
| 6 | (S-endo) 1,7,7-trimethylnorbornyl | O—CO | Me (R) | H | 1 | 2-methyl-1-hydroxy-indanyl |
| 7 | 2-adamantyl | O—CO | Me (R,S) | H | 1 | R,S tetralinyl |
| 8 | 2-adamantyl | O—CO | Me (R,S) | H | 1 | R,S tetralinyl |
| 27 | 2-adamantyl | O—CO | Me | H | 1 | indanyl |

TABLE I-continued $$R^1-A-NH-\underset{+}{\underset{|}{C}}(R^2)(CH_2-\text{indolyl})-CO-(N)_w-Ar^2$$

| Example Number | R¹ | A | R² | R⁹ | w | Ar² |
|---|---|---|---|---|---|---|
| 28 | (2-methyladamantyl) | O—CO | Me | H | 1 | (indanyl) |
| 29 | (S-endo bornyl, Me,Me,Me,H) | O—CO | Me (S) | Null | 0 | (tetrahydroisoquinolinyl) |

In addition to the compounds of Table I the compounds of the present invention include compounds of formula I wherein the indole moiety is a 2- or 3-indolyl.

The compounds include solvates and hydrates and pharmaceutically acceptable salts of the compounds of formula I.

The compounds of the present invention can have multiple chiral centers including those designated in the above formula I by an +, depending on their structures. Centers of asymmetry may exist on substituents R¹, R⁹, and/or Ar². In particular the compounds of the present invention may exist as diastereomers, mixtures of diastereomers, or as the mixed or the individual optical enantiomers. The present invention contemplates all such forms of the compounds. The mixtures of diastereomers are typically obtained as a result of the reactions described more fully below. Individual diastereomers may be separated from mixtures of the diastereomers by conventional techniques such as column chromatography or repetitive recrystallizations. Individual enantiomers may be separated by convention method well known in the art such as conversion to a salt with an optically active compound, followed by separation by chromatography or recrystallization and reconversion to the nonsalt form.

The compounds of the present invention can be formed by coupling individual substituted α-amino acids by methods well known in the art. (See, for example, standard synthetic methods discussed in the multi-volume treatise "The Peptides, Analysis, Synthesis, Biology," by Gross and Meienhofer, Academic Press, New York.) The individual substituted alpha amino acid starting materials are generally known or, if not known, may be synthesized and, if desired, resolved by methods within the skill of the art. (Synthesis of racemic [DL]-α-methyl tryptophan methyl ester—see Braña, M. F., et al, *J. Heterocyclic Chem.* 17:829, 1980.)

A key intermediate in the preparation of compounds of formula I is a compound of formula

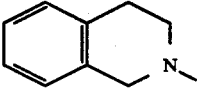

II wherein R is selected from R¹, 9-fluorenylmethyl, Bz and other suitable N-blocking groups. These are useful as intermediates in the preparation of compounds of formula I. The compounds wherein R is 1-adamantyl, 2-adamantyl, 4-protoadamantyl, exo bornyl, endo-bornyl, exo-norbornyl, endo-norbornyl, 2-methylcyclohexyl, 2-chlorocyclohexyl, or camphoryl are novel and are preferred.

The disclosure of U.S. Pat. No. 4,757,151 is hereby incorporated by reference. It describes the 9-fluorenylmethyl blocking group.

Compounds of formula II are prepared by reacting

ROH      III wherein R is as defined above, with phosgene or a phosgene substitute to produce a corresponding compound of formula ROCOCl      IV and then reacting a compound of formula IV with α-methyltryptophan to produce the desired compound of formula II above.

Alternatively, a compound of formula IV can be reacted with an α-methyltryptophan methyl ester to produce

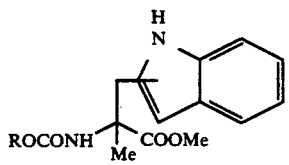

V which can be converted to a compound of formula II by known means such as hydrolysis with aqueous lithium hydroxide.

Scheme I below illustrates procedures for preparing intermediates useful in producing final products of formula I.

Key intermediate (2) is prepared from the alcohol form of a radical selected from 1-adamantyl, 2-adamantyl, 4-protoadamantyl, 9-fluorenylmethyl, exobornyl, endo-bornyl, exo-norbornyl, endo-norbornyl, 2-methylcyclohexyl, 2-chlorocyclohexyl, and camphoryl. The alcohol is dissolved in a solvent such as methylene chloride. It is then converted to the corresponding chloroformate by reaction with bis(trichloromethyl) carbonate in pyridine at about 0° C. The product is formed by condensation with an amine such as α-methyl-D-tryptophan methyl ester. The reaction is carried out in a solvent such as THF to produce, for example, N-[(2-adamantyloxy)carbonyl]-α-methyl-D-tryptophan methyl ester. This is then treated with lithium hydroxide and stirred at room temperature overnight to produce the corresponding carboxylic acid. This novel key intermediate (2) is useful in the production of compounds of formula I as described hereinafter in Schemes II and III.

Schemes IV through VIII correspond to Examples 7 through 17 and illustrate methods of preparing final products of formula I of the instant invention.

SCHEME I
INTERMEDIATES

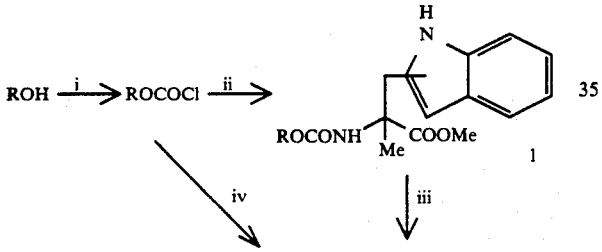

-continued
SCHEME I

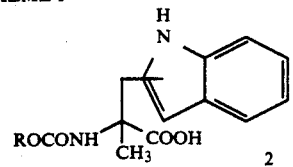

i. COCl₂, disphosgene or triphosgene, pyridine
ii. α-methyl tryptophan methylester
iii. LiOH, aq. 1,4 dioxan
iv. α-methyl tryptophan

SCHEME II

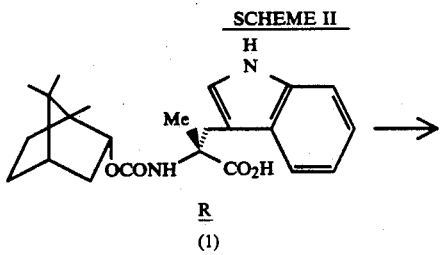

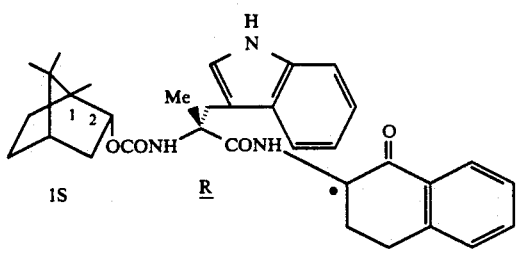

Isomer I. Example 2
Isomer II. Example 3

SCHEME III

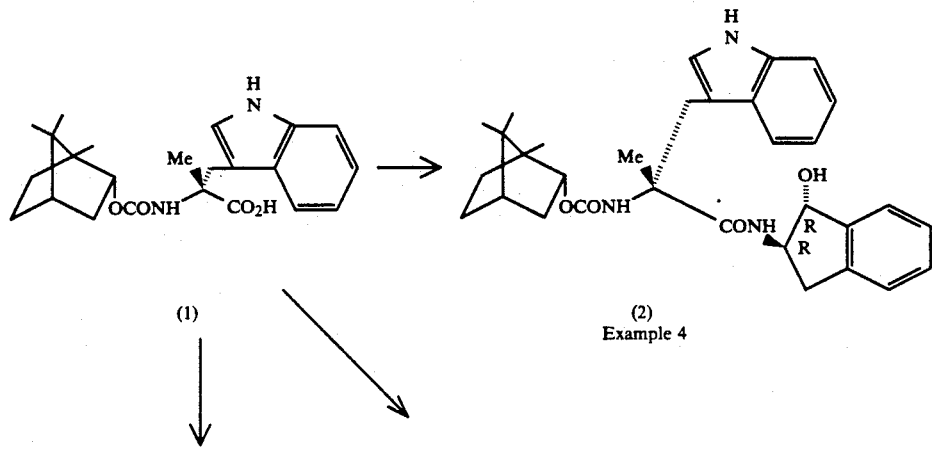

SCHEME III
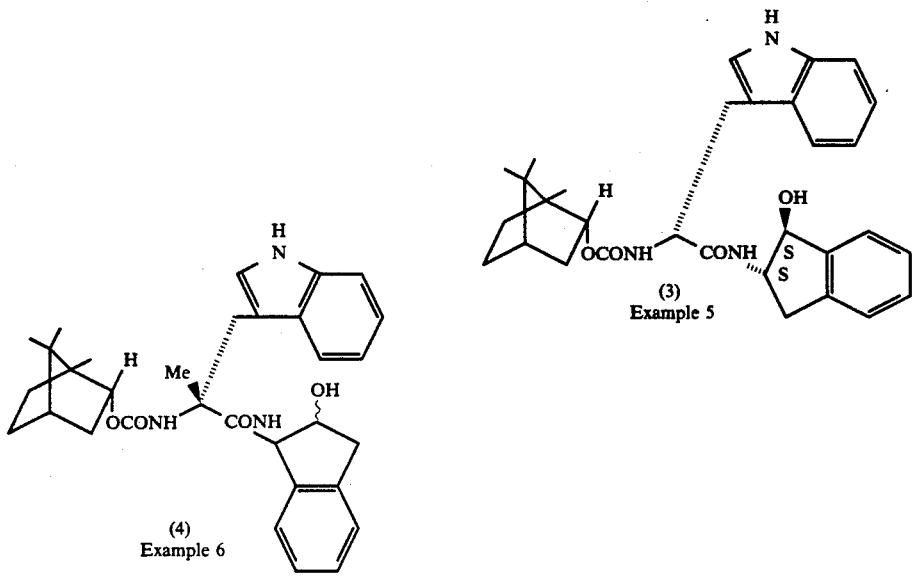
SCHEME IV
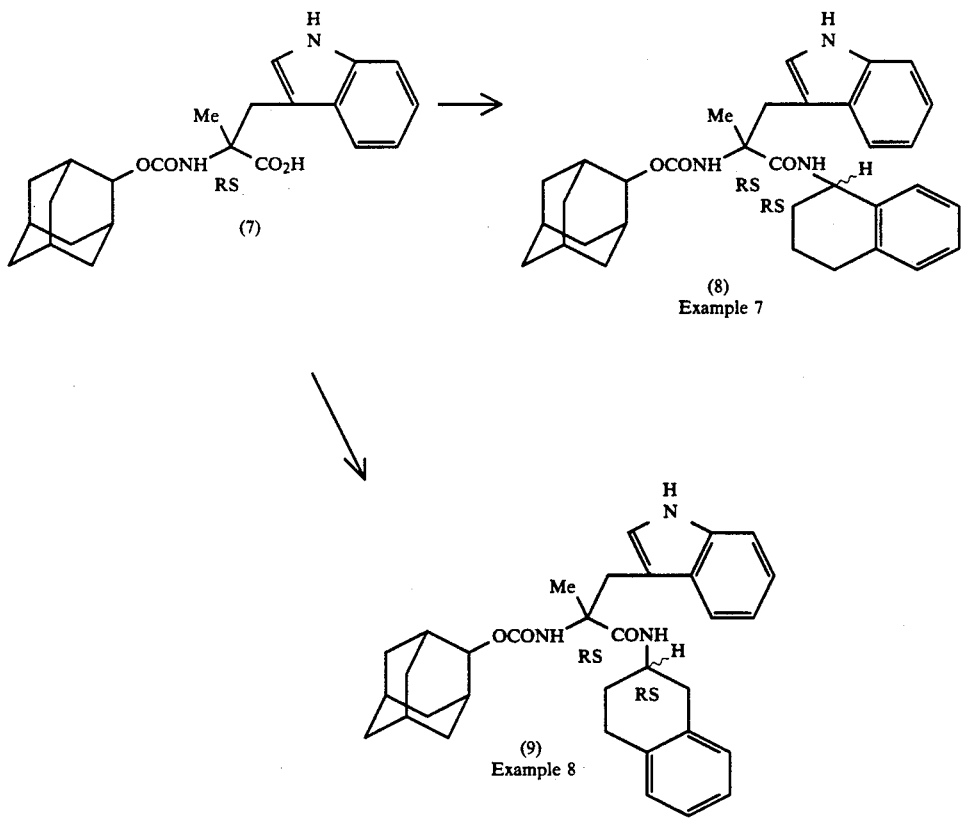

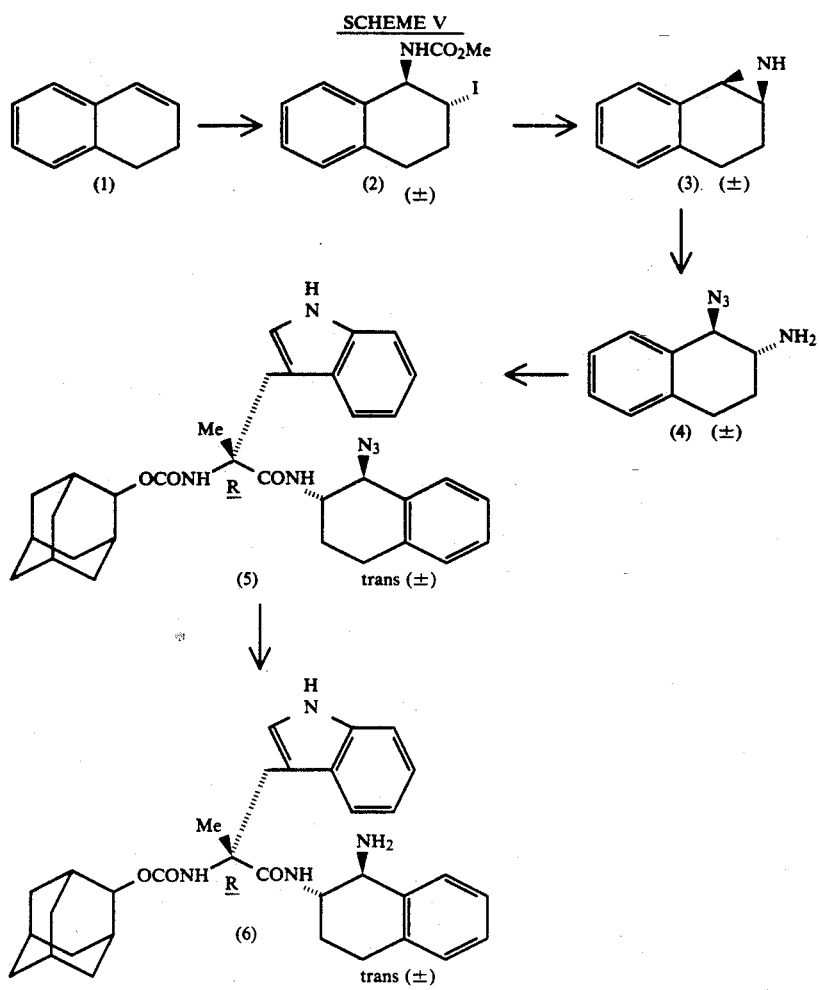

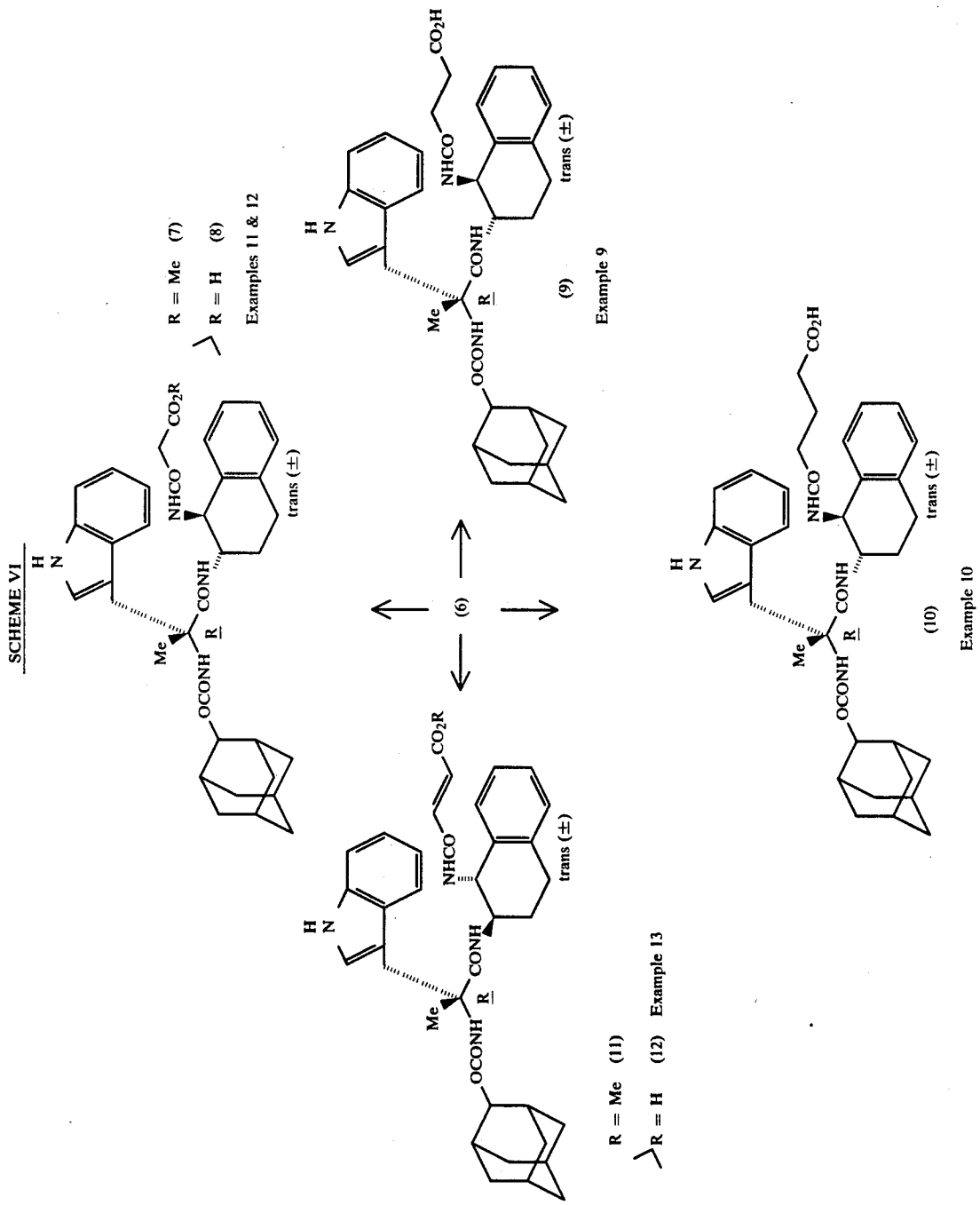

SCHEME VII
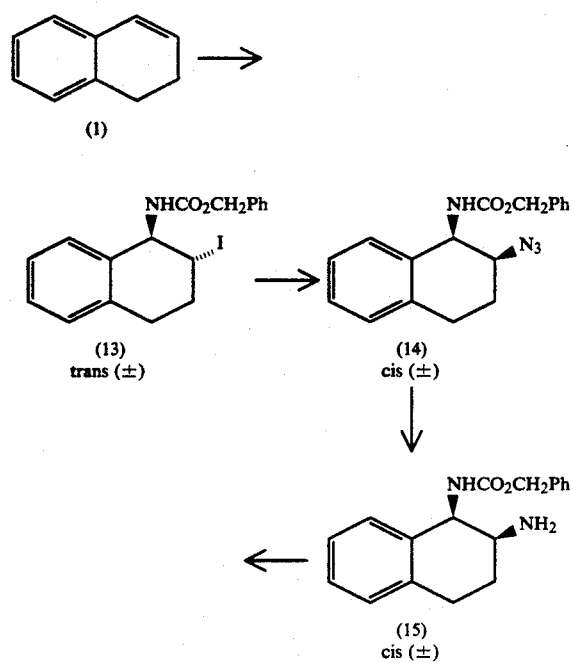
-continued
SCHEME VII
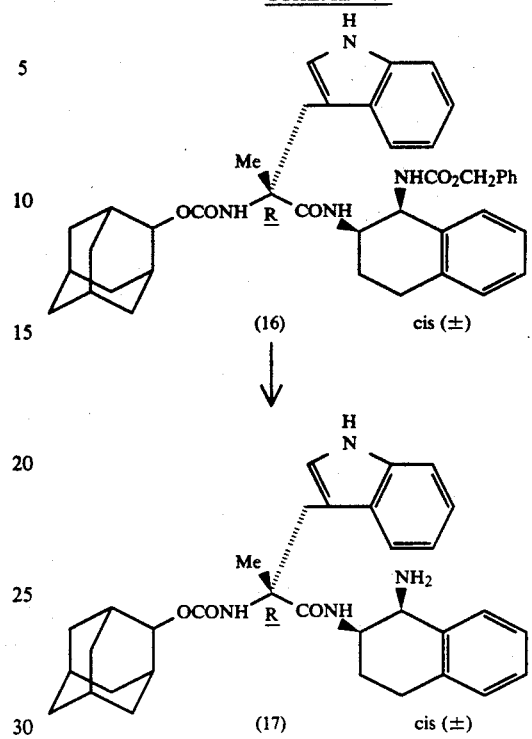

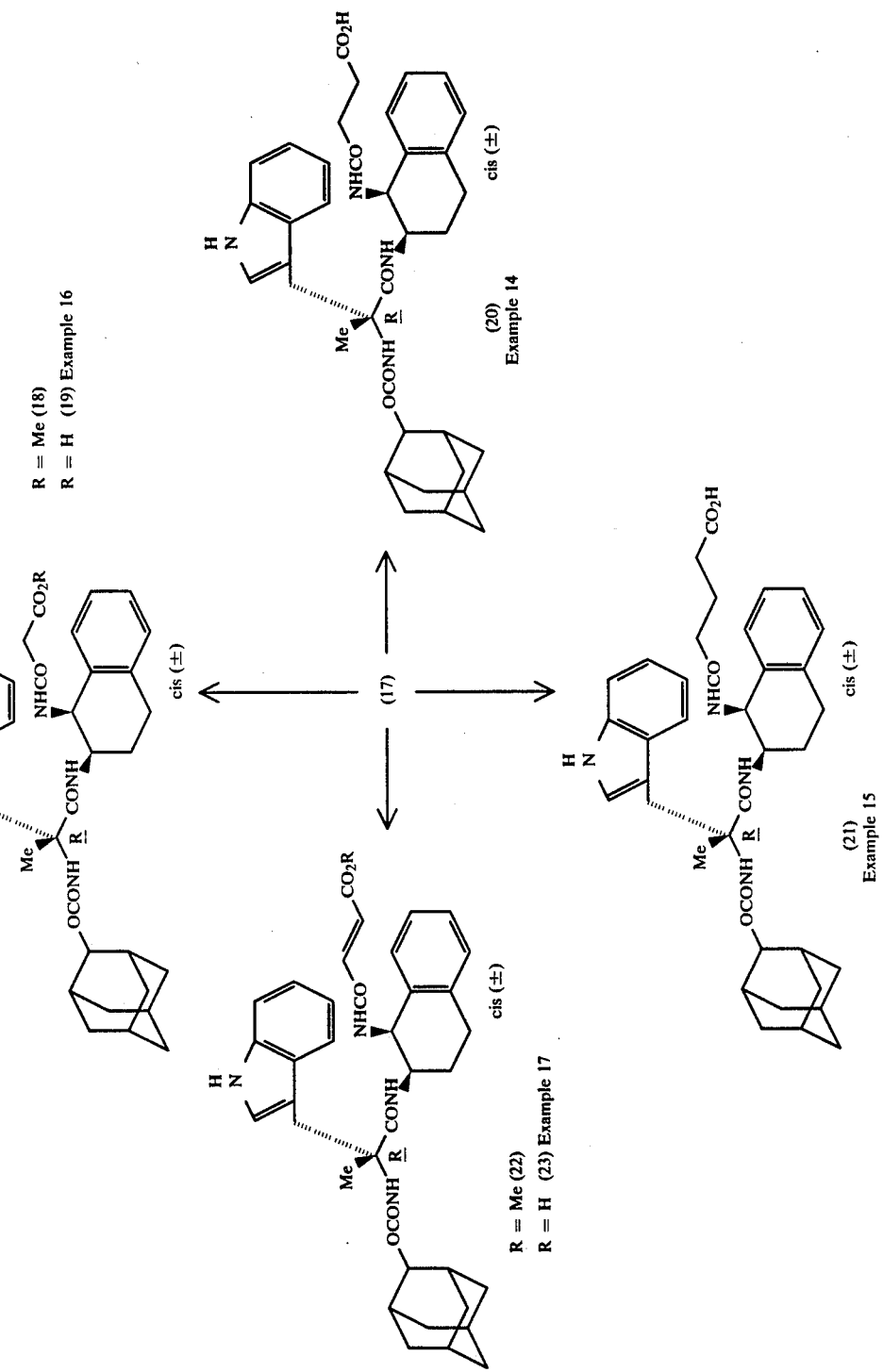

Whenever R in intermediate of formula II is other than $R^1$, it may be removed at an appropriate point in the synthesis by methods known in the art for each respective group and the desired $R^1$ substituted therefore.

BIOLOGICAL ACTIVITY

The biological activity of compounds of the present invention was evaluated employing an initial screening test which rapidly and accurately measured the binding of the tested compound to known CCK receptor sites. Specific CCK receptors have been shown to exist in the central nervous system. (See Hays et al, *Neuropeptides* 1:53–62, 1980; and Satuer et al, *Science* 208:1155–1156, 1980.

In this screening test, the cerebral cortices taken from male CFLP mice weighing between 30–40 g were dissected on ice, weighed, and homogenized in 10 volumes of 50 mM Tris-HCl buffer (pH 7.4 at 0°–4° C.). The resulting suspension was centrifuged, the supernate was discarded, and the pellet was washed by resuspension in Tris-HCl buffer followed by recentrifugation. The final pellet was resuspended in 20 volumes of 10 nM Hepes buffer (pH 7.2 at 23° C.) containing 130 mM NaCl, 4.7 nM KCl, 5 nM $MgCl_2$, 1 nM EDTA, 5 mg/mL bovine albumin, and bacitracin (0.25 mg/ml).

In saturation studies, cerebral cortical membranes were incubated at 23° C. for 120 minutes in a final volume of 500 μliter of Hepes incubation buffer (pH 7.2) together with 0.2–20 nM tritiated-pentagastrin (Amersham International, England).

In the displacement experiments, membranes were incubated with a single concentration (2 nM) of ligand, together with increasing concentrations ($10^{-11}$ to $10^{31}$ 14M) of competitive test compound. In each case, the nonspecific binding was defined as that persisting in the presence of the unlabeled octapeptide $CCK_{26-33}$ ($10^{-6}M$).

Following incubation, radioactivity bound to membranes was separated from that free in solution by rapid filtration through Whatman GF/B filters and washed three times with 4 mL of ice cold Tris-HCl buffer. Filters from samples incubated with tritiated-pentagastrin were placed in polyethylene vials with 4 mL of scintillation cocktail, and the radioactivity was estimated by liquid scintillation spectrometry (efficiency 47–52%).

The specific binding to CCK receptor sites was defined as the total bound tritiated-pentagastrin minus the amount of tritiated-pentagastrin bound in the presence of $10^{-6}$ octapeptide, CCK26-33.

Saturation curves for specific tritiated-pentagastrin binding to mouse cortical membranes were analyzed by the methods of Scatchard (*Ann. New York Acad. Sci.* 51:660–672, 1949, and Hill (*J. Physiol.* 40:IV–VIII, 1910, to provide estimates for the maximum number of binding sites ($B_{max}$) and the equilibrium dissociation constant ($K_a$).

In displacement experiments, inhibition curves were analyzed by either logit-log plots or the iterative curve fitting computer program ALLFIT (DeLean, Munson and Redbard, 1978) to provide estimates of the $IC_{50}$ and nH (apparent Hill coefficient) values. ($IC_{50}$ values were defined as the concentration of test compound required to produce 50% inhibition of specific binding.)

The inhibition constant ($K_i$) of the test compound was then calculated according to the Cheng-Prusoff equation:

$$K_i = \frac{IC_{50}}{1 + [L]/K_a}$$

where [L] is the concentration of radiolabel and $K_a$ is the equilibrium dissociation constant.

The $K_i$ values for several representative compounds of the present invention are present in Table II below.

TABLE II

| | Binding Data | |
|---|---|---|
| Compound Number | $K_i$ (nM) CCK B | $K_i$ (nM) CCK A |
| 1 | 280 | N.T. |
| 2 | 111 | 5300 |
| 3 | 30 | 3870 |
| 4 | 94 | 7620 |
| 5 | 59 | N.T. |
| 6 | 45 | 5220 |
| 7 | 330 | N.T. |
| 8 | 450 | N.T. |

N.T. = Not tested
Compound numbers are from the list of compounds starting on page 17.

Compounds of the present invention are expected to be useful as appetite suppressants as based on the tests described hereinbelow.

In the Palatable Diet Feeding assay, adult male Hooded Lister rats weighing between 200–400 g are housed individually and trained to eat a palatable diet. This diet consists of Nestlés sweetened condensed milk, powdered rat food and rat water which when blended together set to a firm consistency. Each rat is presented with 20–30 g of the palatable diet for 30 minutes per day during the light phase of the light-dark cycle over a training period of five days. The intake of palatable diet is measured by weighing the food container before and after the 30-minute access period (limits of accuracy 0.1 g). Care is taken to collect and correct for any spillage of the diet. Rats have free access to pellet food and water except during the 30-minute test period.

After the training period, dose-response curves are constructed for CCK8 for several representative compounds of the present invention (n = 8–10 rats per dose level). $MPE_{50}$ values ($\pm 95\%$ confidence limits) are obtained for the anorectic effects of these compounds.

In therapeutic use as appetite suppression agents, the compounds of the instant invention are administered to the patient at dosage levels of from about 200 to about 2800 mg per day.

Male Hooded Lister rats (175–250 g) are housed individually and fasted overnight (free access to water). They are anesthetized with urethane (1.5 g/kg IP) and the trachea cannulated to aid spontaneous respiration. The stomach is perfused continuously using a modification of the original method of Ghosh & Schild in "Continuous recording of acid secretion in the rat", *Brit. J. Pharmac.* 13:54 61, 1956 as described by Parsons in "Quantitative studies of drug-induced gastric acid secretion". (Ph.D. Thesis, University of London, 1969). The cavity of the stomach is perfused at a rate of 3 mL/min with 5.4% w/v glucose solution through both the esophageal and body cannula. The fluid is propelled by a roller pump (Gilson, Minipuls 2), through heating coils to bring its temperature to 37°±1° C. The perfusion fluid is collected by the fundic collecting funnel and passed to a pH electrode connected to a Jenway pH meter (PHM6). An output is taken from the pH meter to a Rikadenki chart recorder for the on-line recording of the pH of the gastric perfusate.

Pentagastrin is stored as a frozen aliquot and diluted to the required concentrations with sterile 0.9% w/v NaCl. Novel compounds are dissolved in sterile 0.9% w/v NaCl on the day of the experiment. Drugs are administered IV through a cannulated jugular vein as a bolus in a dose volume of 1 ml/kg washed in with 0.15 ml 0.9% w/v NaCl. Basal pH is allowed to stabilize before administration of compounds is begun. Typically 30 minutes elapses between surgery and the first compound administration.

With test compounds, the antagonism is expected to be reversible with full recovery of the response to pentagastrin.

The compounds of the instant invention are also expected to be useful as antiulcer agents as discussed hereinbelow.

Aspirin induced gastric damage is assessed in groups of 10 rats each.

All animals are fasted for 24 hours before and throughout the experiment. Drug or vehicle are given 10 minutes before an oral dose of 1 ml of a 45-mg/mL suspension of aspirin in 0.5% carboxymethylcellulose (CMC).

The animals are sacrificed 5 hours after aspirin administration and the stomachs removed and opened for examination.

Gastric damage was scored as follows:

| Score | |
|---|---|
| 1 | Small hemorrhage |
| 2 | Large hemorrhage |
| 3 | Small ulcer |
| 4 | Large ulcer |
| 5 | Perforated ulcer |

The specific dosages employed, however, may be varied depending upon the patient, the severity of the condition being treated, and the activity of the compound employed. Determination of optimum dosages is within the skill of the art.

The compounds of the instant invention are also expected to be useful as anxiolytic agents as described and discussed below.

Anxiolytic activity is assessed in the light/dark exploration test in the mouse (B. J. Jones, et al, *Brit. J. Pharmac.* 93:985-993, 1988).

The pretreatment time is 40 minutes. The compound is given p.o. in 0.1, 1, and 10 mg/kg doses.

The apparatus is an open topped box, 45 cm long, 27 cm wide, and 27 cm high, divided into a small (2/5) area and a large (3/5) area by a partition that extended 20 cm above the walls. There is a 7.5×7.5 cm opening in the partition at floor level. The small compartment is painted black and the large compartment white. The floor of each compartment is marked into 9 cm squares. The white compartment is illuminated by a 100-watt tungsten bulb 17 cm above the box and the black compartment by a similarly placed 60-watt red bulb. The laboratory is illuminated with red light.

All tests are performed between 13 hundred hours, 0 minutes and 18 hundred hours, 0 minutes. Each mouse is tested by placing it in the center of the white area and allowing it to explore the novel environment for 5 minutes. Its behavior is recorded on videotape and the behavioral analysis was performed subsequently from the recording. Five parameters are measured: the latency to entry into the dark compartment, the time spent in each area, the number of transitions between compartments, the number of lines crossed in each compartment, and the number of rears in each compartment.

In this test an increase in the time spent in the light area is a sensitive measure of, that is directly related to, the anxiolytic effects of several standard anxiolytic drugs. Drugs are dissolved in water or saline and administered either subcutaneously, intraperitoneally, or by mouth (PO) via a stomach needle.

The compounds of the instant invention are useful as antipsychotic agents. Compounds are tested for their ability to reduce the effects of intra-accumbens amphetamine in the rat as described hereinafter.

Male Sprague Dawley (CD) Bradford strain rats are used. The rats are housed in groups of five at a temperature of 21°±2° C. on a 12 hour light-dark cycle of lights-on between 07 hours 00 minutes and 20 hours 00 minutes. Rats are fed CRM diet (Labsure) and allowed water ad libitum.

Rats are anesthetized with chloral hydrate (400 mg/kg SC) and placed in a Kopf stereotaxic frame. Chronically indwelling guide cannulae (constructed of stainless steel tubing 0.65 mm diameter held bilaterally in Parspex holders) are implanted using standard stereotaxic techniques to terminate 3.5 mm above the center of the nucleus accumbens (Ant. 9.4, Vert. 0.0, Lat. 1.6) or 5.0 mm above the central nucleus of the amygdala (Ant. 5.8, Vert. −1.8, Lat. ±4.5) (atlas of De Groot, 1959). The guides are kept patent during a 14-day recovery period using stainless steel stylets, 0.3 mm diameter, which extended 0.5 mm beyond the guide tips.

Rats are manually restrained and the stylets removed. Intracerebral injection cannulae, 0.3 mm diameter, are inserted and drugs delivered in a volume of 0.5 $\mu$L over 5 seconds (a further 55 seconds was allowed for deposition) from Hamilton syringes attached via polythene tubing to the injection units. Animals are used on a single occasion only.

Behavioral experiments are conducted between 07 hours 30 minutes and 21 hours 30 minutes in a quiet room maintained at 22°±2° C. Rats are taken from the holding room and allowed one hour to adapt to the new environment. Locomotor activity is assessed in individual screened Perspex cages (25×15×15 cm (high) (banked in groups of 30) each fitted with one photocell unit along the longer axis 3.5 cm from the side; this position has been found to minimize spurious activity counts due to, for example, preening and head movements when the animal is stationary. Interruptions of the light beam are recorded every 5 minutes. At this time animals are also observed for the presence of any nonspecific change in locomotor activity, e.g., sedation, prostration, stereotyped movements, that could interfere with the recording of locomotor activity.

The abilities of compounds to inhibit the hyperactivity caused by the injection of amphetamine into the nucleus accumbens of the rat is measured.

An increase in locomotor activity followed the bilateral injection of amphetamine (20 $\mu$g) into the nucleus accumbens; peak hyperactivity (50 to 60 counts 5 minutes$^{-1}$) occurs 20 to 40 minutes after injection. Intraperitoneal injection of the rats with a compound (20 mg/kg or 30 mg/kg) or (10 mg/kg) reduces the hyperactivity caused by the intra-accumbens injection of amphetamine. This test is known to be predictive of antipsychotic activity (Costall, Domeney & Naylor & Tyers, *Brit. J. Pharmac.* 92:881-894).

The compounds of the instant invention are expected to prevent and treat the withdrawal response produced when chronic treatment by a drug is stopped or when alcohol abuse is stopped. These compounds are therefore useful as therapeutic agents in the treatment of chronic drug or alcohol abuse.

The effect of the compounds of the instant invention is illustrated, for example, in the mouse "light/dark box" test.

Five animals are given nicotine, typically in a range of 0.01 to 100 mg/kg i.p. b.d. for 14 days. After a 24-hour withdrawal period, a compound is given typically at a range of 0.01 to 100 mg/kg i.p. b.d. The increased time spent in the light area is a sensitive measure of the effect of the compound as an agent to treat withdrawal effects from nicotine.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5 to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

A preferred pharmaceutically acceptable salt is the N-methyl glucamine salt.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

Examples are illustrative of methods of preparing the final products.

EXAMPLES

EXAMPLE 1

Carbamic acid,
[1-(1H-indol-3-ylmethyl)-1-methyl-2-oxo-2-(1,2,3,4-tetrahydro-2-isoquinolinyl)ethyl]-,
tricyclo[3.3.1.1$^{3,7}$]dec-2-yl ester, (R)-

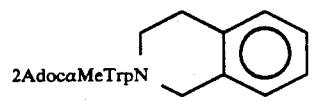

2AdocaMeTrpN

To a stirred solution of α-methyl-N-[(tricyclo[3.3.1.1$^{3,7}$]dec-1-yloxy)carbonyl]-R-tryptophan (150 mg, 0.3 mmol) in anhydrous EtOAc (7 mL) was added N,N-dicyclohexylcarbodiimide (86 mg, 0.41 mmol) and pentafluorophenol (77 mg, 0.41 mmol). The reaction mixture was stirred at room temperature for 2 hours and then 1,2,3,4-tetrahydroisoquinoline (51 mg, 0.38 mmol) in EtOAc (2 mL) added. After stirring for 3 days, the reaction mixture was filtered and the filtrate concentrated in vacuo. The residue was chromatographed over reverse phase silica using 4:1 MeOH:H$_2$O as eluant to give the desired amide as an amorphous solid (83 mg, 43%); m.p. 95°-100° C.; IR (film) 3300, 2908, 2854, 1696, and 1625 cm$^{-1}$; NMR (CDCl$_3$) δ 1.40-1.90 (17H, m), 2.85 (2H, t, J 6 Hz), 3.50 (2H, m), 3.95 (2H, br s), 4.75 (1H, m), 4.85 (2H, br s), 5.15 (1H, br s), 6.97 (1H, s), 7.10 (6H, m), 7.34 (1H, d, J 8 Hz), 7.56 (1, d, J 8 Hz), 8.15 (1H, s); Anal. (C$_{32}$H$_{37}$N$_3$O$_3$.0.5CHCl$_3$), C, H, N.

EXAMPLES 2 AND 3

Carbamic acid,
[1-(1H-indol-3-ylmethyl)-1-methyl-2-oxo-2-[(1,2,3,4-tetrahydro-1-oxo-2-naphthalenyl)-amino]ethyl]-,
1,7,7-trimethylbicyclo[2.2.1.1]hept-2-yl ester; (Bicyclo system 1S-endo: TRP center R; naphthyl center (+) and (-))

1-S-endoBornyloxycarbonyl-α-methyl-R-tryptophan (247 mg, 0.62 mmol) and pentafluorophenol (114 mg, 0.62 mmol) as a solution in EtOAc (15 mL) was treated with dicyclohexylcarbodiimide (130 mg, 0.63 mmol) at 0° C. and left 24 hours at 4° C. The mixture was then filtered and the filtrate added to a stirred mixture of 2-amino-1-tetralone HCl salt (122 mg, 0.62 mmol) and triethylamine (63 mg, 0.62 mmol) in EtOAc (10 mL) at 0° C. The combined mixture was left stirring at room temperature for 18 hours before 4-dimethylamino pyridine (20 mg, 0.16 mmol) was added and the mixture left a further 48 hours. The reaction mixture was then washed with H$_2$O (10 mL), 1M HCl (10 mL), and H$_2$O (10 mL). The organic phase was dried over MgSO$_4$ and concentrated in vacuo. The residue was chromatographed over silica gel twice, once using 1% MeOH in CH$_2$Cl$_2$, then the two diastereoisomers were separated using 25% EtOAc in n-hexane as eluants, to give Isomer I as a white solid (110 mg, 33%), and Isomer II as a noncrystalline solid (100 mg, 30%).

EXAMPLE 2

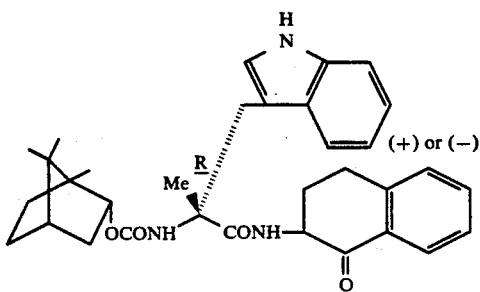

Isomer I m.p. 106°–112° C. (MeOH/H$_2$O); [α]20D +33.2° (c=0.27, MeOH); IR (film) 1699 and 1663 cm$^{-1}$; NMR (CDCl$_3$) 0.82 (3H, s), 0.85 (3H, s), 0.90 (3H, s), 1.07 (1H, dd, J 13.5 and 3 Hz), 1.20–1.30 (2H, m), 1.64 (3H, s), 1.65–1.90 (4H, m), 2.30–2.45 (1H, m), 2.75–2.79 (1H, m), 2.98 (1H, br d, J 16 Hz), 3.20–3.35 (1H, m), 3.43 (1H, d, J 14 Hz), 3.51 (1H, d, J 14 Hz), 4.56 (1H, dt, J 13.5 and 5 Hz), 4.70–5.00 (1H, br), 4.90 (1H, br d, Hz), 5.37 (1H, br s), 7.05–7.40 (7H, m), 7.51 (1H, t, J 7 Hz), 7.61 (1H, d, J 8 Hz), 7.98 (1H, d, J Hz), 8.20 (1H, s); Anal. C$_{33}$H$_{39}$N$_3$O$_4$.0.75H$_2$O; C, H, N.

EXAMPLE 3

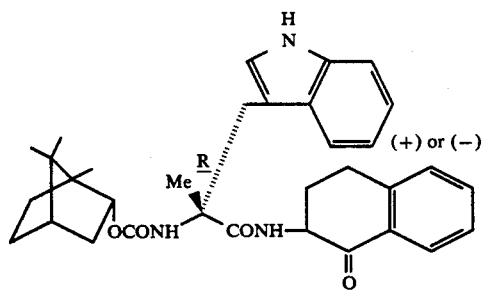

Isomer II m.p. 106°–111° C.; [α]20D −12° (c =0 1, MeOH); IR (film) 1697 and 1662 cm$^{-1}$; NMR (CDCl$_3$) δ 0.85 (6H, s), 0.89 (3H, s), 1.03 (1H, dd, J 14 and 3 Hz), 1.10–1.30 (2H m), 1.61 (3H, s), 1.65–1.90 (4H, m), 2.30 2.40 (1H, m), 2.65–2.75 (1H, m), 2.96 (1H, br d, J 16 Hz), 3.20–3.30 (1H, m), 3.41 (1H, d, J 15 Hz), 3.49 (1H, d, J 15 Hz), 4.57 (1H, dt, J 14 and 5 Hz), 4.89 (1H, d, J 9 Hz), 5.37 (1H, br s), 7.00–7.40 (8H, m), 7.53 (1H, dt, J 7 and 1 Hz), 7.60 (1H, d, J 8 Hz), 7.96 (1H, 0, J 8 Hz), 8.18 (1H, br s); Anal. C$_{33}$H$_{32}$N$_3$O$_4$m 0.5 Hz; C, H, N.

EXAMPLE 4

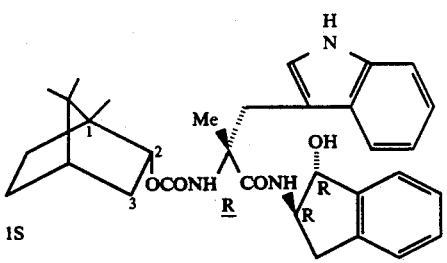

A solution of the acid (Schemes II or III, No. 1) (199 mg, 0.50 mmol) and pentafluorophenol (92 mg, 0.5 mmol) in EtOAc (20 mL) was cooled to 0° C. and a solution of N,N'-dicyclohexylcarbodiimide (108 mg, 0.525 mmol) in EtOAc (5 mL) was added. This was stirred for 24 hours at 0° C., filtered, and trans-2(R)amino 1-(R)hydroxy indane (75 mg, 0.5 mmol) added. This mixture was stirred at room temperature for 24 hours and then the solvent was removed in vacuo. The residue was chromatographed using 2% MeOH in CH$_2$Cl$_2$ as eluant to give the product as a white solid (191 mg, 72%), m.p. 100°–103° C. (MeOH/H$_2$O); IR (film) 3368, 2954, 1696, and 1651 cm$^{-1}$; NMR (CDCl$_3$) δ 0.82 (3H, s), 0.86 (3H, s), 0.90 (3H, s), 0.97 (1H, dd, J 14 and 3 Hz), 1.05–1.35 (2H, m), 1.63 (3H, s), 1.65–1.90 (3H, m), 2.30–2.40 (1H, m), 2.60 (1H, dd, J 15 and 8.5 Hz), 3.15 (1H, dd, J 15 and 8.5 Hz), 3.30 (1H, d, J 15 Hz), 3.53 (1H, d, J 15 Hz), 4.15–4.25 (1H, m), 4.70–4.80 (1H, br s), 4.89 (1H, d, J 10 Hz), 4.98 (1H, d, J 6.5 Hz), 5.16 (1H, brs), 6.75–6.85 (1H, brs), 7.07 (1H, d, J 2 Hz), 7.10–7.40 (7H, m), 7.62 (1H, d, J 8 Hz), 8.17 (1H, s); MS (FAB) m/e 3321.1 (100), 530 (83). Anal. C$_{32}$H$_{39}$N$_3$O$_4$.0.25H$_2$O; C, H, N.

EXAMPLE 5

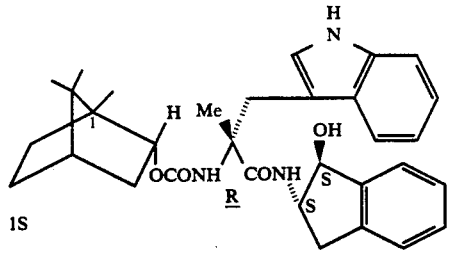

Method exactly as for Example 4 (Scheme III No. 2), except using trans 2(S) amino 1(S) hydroxy indane: yield 157 mg, 85%); m.p. 97–103° C. (MeOH/H$_2$O); IR (film) 3369, 2954, 1696, and 1659 cm$^{-1}$; NMR (CDCl$_3$) δ 0.76 (3H, s), 0.82 (3H, s), 0.88 (3H, s), 0.94–1.00 (1H, m), 1.10–1.30 (2H, m), 1.55 (3H, s), 1.60–1.80 (3H, m), 2.20–2.37 (1H, m), 2.60 (1H, brs), 2.77 (1H, dd, J 15.5 and 7 Hz), 3.12 (1H, dd, J 15.5 and 7 Hz), 3.38 (1H, d, J 15 Hz), 3.51 (1H, d, J 15 Hz), 4.60–4.70 (1H, m), 4.71 (0.5H, brs), 4.81 (0.5H, brs), 5.03 (1H, g, J 5 Hz), 5.08 (1H, s), 6.48 (1H, d, J 8 Hz), 7.00–7.40 (8H, m), 7.62 (1H, d, J 8 Hz), 8.1 (1H, brs); Anal. C$_3$zH39N3O4.0.25H20; C, H, N.

EXAMPLE 6

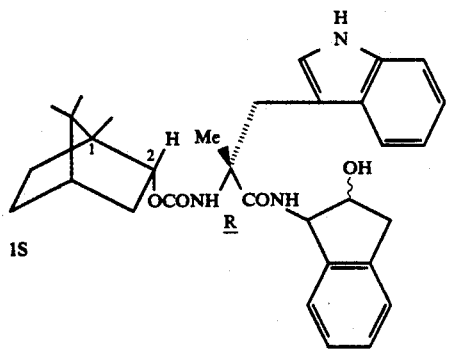

Method exactly as for Example 4 (Scheme III No. 2) except using 1-amino-2-hydroxyindane, yield 183 mg, 69% m.p. 99°–106° C. (MeOH/H₂O); IR (film) 3339, 1699, and 1657 cm$^{-1}$; NMR (CDCl₃) δ 0.81 (3H, 2xs, separation Hz), 0.85 (3H, s), 0.89 (3H, 2xs, separation 2 Hz), 0.90–1.00 (1H, m), 1.10–7.35 (2H, m), 1.60–1.85 (6H, m), 2.30–2.40 (1H, m), 2.85–2.95 (1H, m), 3.20 3.60 (3H, m), 4.20–4.30 (1H, m), 4.38 (0.5H, s), 4.50 (0.5H, s), 4.85–4.93 (1H, m), 5.07 (1H, q, J 7 Hz), 5.18 (0.5H, s), 5.28 (0.5H, s), 6.65 (1H, d, J 5.5 Hz), 6.80 (0.5H, d, J 7.5 Hz), 6.85 (0.5H, d, J 7.5 Hz), 7.05–7.25 (6H, m), 7.37 (1H, d, J 8 Hz), 7.62 (1H, d, J 8 Hz), 8.24 (1H, brs); Anal. $C_{32}H_{39}N_3O_4 \cdot 0.5H_2O$; C, H, N.

EXAMPLE 7

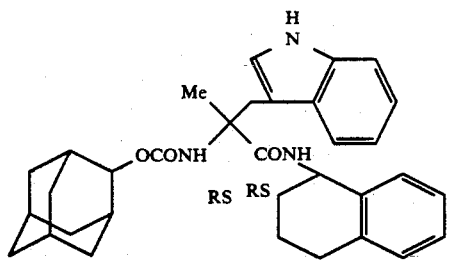

Method exactly as for Example 4, except using 2Adoc-α-Me-RS-TrpOH (7) and 1-aminotetralin; yield mg, 87%; m.p. 108°–116° C. (MeOH/H₂O); IR (film) 3400–3200, 2907, 2855, 1704, 1652, and 1493 cm$^{-1}$; NMR (CDCl₃) δ 1.45–1.55 (2H, m), 1.59 (3H, s), 1.70–2.05 (16H, m), 2.70–2.80 (2H, m), 3.36 (0.5H, d, J 14.5 Hz), 3.37 (0.5H, d, J 14.5 Hz), 3.54 (0.5H, d, J 14.5 Hz), 3.57 (0.5H, d, J 14.5 Hz), 5.05–5.15 (1H, m), 5.16 (0.5H, s), 5.19 (0.5H, s), 6.34 (0.5H, d, J Hz), 6.38 (0.5H, d, J 6 Hz), 7.00–7.25 (7H, m), 7.3 H, d, J 8 Hz), 7.63 (1H, d, J 8 Hz), 8.17 (1H, s); MS (FAB) m/e 526.3 (100, 396.1 (33), 33.1 (31); Anal. $C_{33}H_{39}N_3O_3 \cdot 0.25H_2O$; C, H, N.

EXAMPLE 8

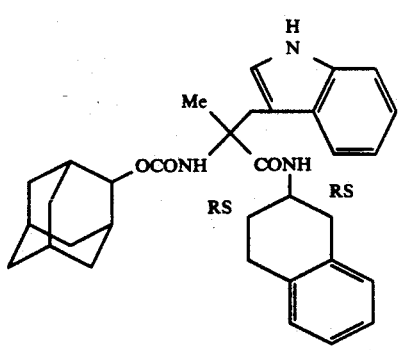

Method exactly as for Example 4, except using 2-Adoc-α-Me-RS-TrpOH (7) and 2-aminotetralin; yield 210 mg, 795, m.p. 97°–101° C. (MeOH/H₂O); IR (film) 3400–3200, 2911, 2855, 1700, 1651, and 1495 cm$^{-1}$; NMR g(CDCl₃) δ 1.50–2.00 (16H, m), 1.57 (1.5H, s), 1.58 (1.5H, s), 2.42 (0.5H, d, J 7.5 Hz), 2.48 (0.5H, d, J 7.5 Hz), 2.70–3.05 (3H, m), 3.27 (0.5H, d, J 14.5 Hz), 3.29 (0.5H, d, J 14.5 Hz), 3.51 (0.5H, d, J 14.5 Hz), 3.54 (0.5H, d, J 14.5 Hz), 4.15–4.25 (1H, m), 4.80 (1H, d), 5.16 (0.5H, s), 5.21 (0.5H, s), 6.10–6.20 (1H, brs), 6.99–7.21 (7H, m), 7.36 (1H, d, J 8 Hz), 7.61 (1H, d, J 8 Hz), 8.12 (1H, s), MS (FAB) m/e 526.3 (100), 396.2 (25), 330.2 (33); Anal. $C_{33}H_{39}N_3O_3 \cdot 0.75H$); C, H, N.

EXAMPLE 9

Butanoic acid, 4-oxo-4-[1,2,3,4-tetrahydro-2-[[3-(1H-indol-3-yl) -2-methyl-1-oxo-2-[[(tricyclo[3.3.1.1$^{3,7}$]-dec-2-yloxy)-carbonyl]amino]propyl]amino]-1-naphthalenyl]amino]-

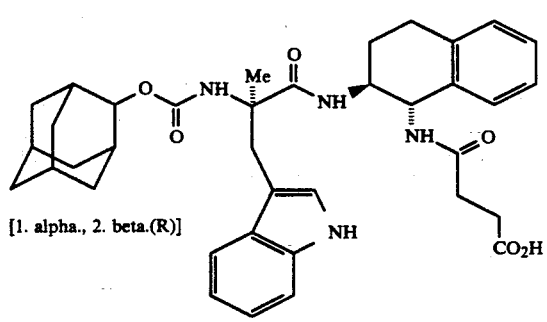

[1. alpha., 2. beta.(R)]

Step 1. Carbamic acid, 2-[(1-azido-1,2,3,4-tetrahydro-2-naphthalenyl)amino]1-(1H-indol 3-yl-methyl)-1-methyl-2-oxoethyl]1-tricyclo[3.3.1.1$^{3,7}$]dec2-yl ester (See Scheme V)

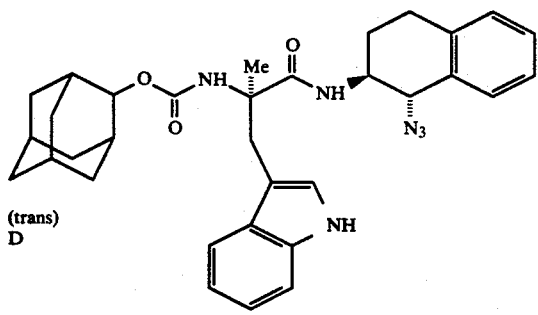

(trans)
D

A solution of 2-adamantyloxycarbonyl-α-methyl-R-tryptophan (3.00 g, 7.57 mmol) and pentafluorophenol (1.39 g, 7.57 mmol) in EtOAc (80 mL) was cooled to 0° C. and treated with N,N'-dicyclohexylcarbodiimide (1.56 g, 7.57 mmol). This reaction mixture was stirred for 30 minutes at 0° C., filtered, and the filtrate treated with (±)trans-2-amino-1-azido-1,2,3,4-tetrahydronaphthalene (1.56 g, 8.32 mmol) and allowed to warm to room temperature. After 48 hours the reaction mixture was washed with 1M citric acid solution (2×2 mL), saturated NaHCO$_3$ solution (2×20 mL), and H$_2$O (2×20 mL). The organic phase was dried over MgSO$_4$ and the solvent evaporated in vacuo. The residue was separated by reverse phase silica gel chromatography using 4:1 MeOH:H$_2$O as eluant to give the product 5 as a noncrystalline white solid (3.71 g, 86%), m.p. 105°-110° C. $[\alpha]_D^{20}$= +39.4° (c=0.5, MeOH); IR (film) 3500-3200, 2909, 2855, 2097, 1702, 1657, and 1493 cm$^{-1}$; NMR (CDCl$_3$) δ 1.40 (1H, s), 1.45 (2.5H, s), 1.55 (1.5H, s), 1.65-1.90 (13H, m), 2.00-2.20 (1H, m), 2.60-2.75 (1H, m), 2.81 (0.5H, b, J 5.4 Hz), 2.87 (0.5H, 5, J 5.3 Hz), 3.17-3.27 (1H, m), 3.49 (0.5H, d, J 14.8 Hz), 3.56 (0.5H, d, J 14.7 Hz), 4.18 (0.5H, d, J 4.6 Hz), 4.25 4.35 (1.5H, m), 4.60-4.70 (1H, m), 5.04 (1H, s), 6.40-6.45 (0.5H, m), 6.46-6.55 (0.5H, m), 6.94 (1H, s), 7.05-7.30 (6H, m), 7.36 (1H, d, J 7.8 Hz), 7.55-7.65 (1H, m), 8.11 (1H, s); MS m/e (FAB) 567 (5), 173 924), 146 (28), 135 (100) and 109 (39).

Step 2. (Scheme V, No. 6)

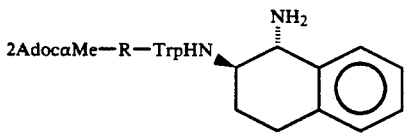

A solution of thiazide from Step 1 (Scheme V, No. 5) (1.20 g, 2.11 mmol) in absolute EtOH (150 mL) was treated with Lundar catalyst (0.6 g, 50% w/w) and put under an atmosphere of hydrogen at a pressure of 50 psi for 12 hours at room temperature. This was then filtered over gypsum and evaporated in vacuo to give the amine as a syrup (1.14 g, 100%). This was used immediately in Step 3.

Step 3.

A solution of the amine from Step 2 (Scheme V, No. 6) (0.2 g, 0.37 mmol) in EtOAc (15 mL) was treated with succinic anhydride (0.044 g, 0.44 mmol) and stirred at reflux with N,N-dimethyl amino pyridine (0.061 g, 0.50 mmol) for 18 hours. This mixture was then evaporated to dryness and the residue chromatographed over reverse phase silica using 5:1; MeOH:H$_2$O as eluent to give the product (Example 1) as a white solid (0.157 g, 66%), m.p. 137°-150° C.; $[\alpha]_D^{20}$=32° (c=0.5, MeOH); IR (film) 3500-3200, 2910, 2856, 1712, 1651, and 1531 cm$^{-1}$; NMR (DMSO-d$_6$+D$_{20}$) δ 1.23 (1.5H, s), 1.29 (1.5H, s), 1.35-1.55 (2H, m), 1.60-2.00 (14H, m), 2.20-2.55 (4H, m), 2.70-2.85 (2H, m), 3.10-3.60 (2H, m), 3.85-4.00 (1H, m), 4.60-4.70 (1H, m), 5.00-5.10 (1H, M), 6.60-6.70 (1H, m), 6.85-7.25 (7H, m), 7.31 (1H, d, J 8 Hz), 7.46 (1H, d, J 8 Hz), 7.30-7.55 (1H, m), 8.23 (1H, d, J 9 Hz); Analysis for C$_{37}$H$_{44}$N$_4$O$_6$: Calcd: C, 67.92; H, 7.00; N, 8.56. Found: C, 67.96; H, 6.87; N, 8.65.

EXAMPLE 10 (Scheme VI, No. 10)

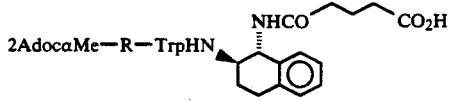

Method exactly as for Example 9 except using glutaric anhydride in Step 3 instead of succinic anhydride, m.p. 130°-142° C.; $[\alpha]_D^{21}$=410.8° (c=0.5, MeOH; IR (film) 3500-3200, 2919, 2854, 1710, 1651, and 1527 cm$^{-1}$; NMR (CDCl$_3$) δ 1.25 (1.5H, s), 1.35 91.5H, s), 1.40 1.55 (2H, m), 1.15-2.05 (16H, m), 2.10-2.25 (2H, m), 2.50-2.55 (4H, m), 2.75-2.85 (2H, m), 3.90-4.05 (1H, m), 4.55-4.70 (1H, m), 5.00-5.10 (1H, m), 6.55 6.70 (1H, m), 6.85-7.15 (7H, m), 7.31 (1H, d, J 8 Hz), 7.45-7.55 (1.5H, m), 7.60-7.65 (10.5H, m), 8.15-8.25 (1H, m).

Examples 11 and 12 (Scheme VI, No. 7a and 7b)

Propanoic acid, 3-[2-[[3-(1H-indol-3-yl)-2-methyl-1-oxo-2-[[(tricyclo[3.3.1.1$^{3,7}$]dec-2-yloxy)carbonyl]-amino]propyl]amino]1,2,3,4-tetrahydro-1-naphthalenyl]amino]3-oxo, methyl ester (Isomer I) and Propanoic acid, 3-[2-[3-1H-indol-3-yl)-2-methyl-1-oxo 2-[(tricyclo3.3.1.1$^{3,7}$]dec-2-yloxy)carbonyl]-amino]-propyl]amino]-1,2,3,4-tetrahydro-1-naphthalenyl-]amino]-3-oxo-, methyl ester (Isomer II)

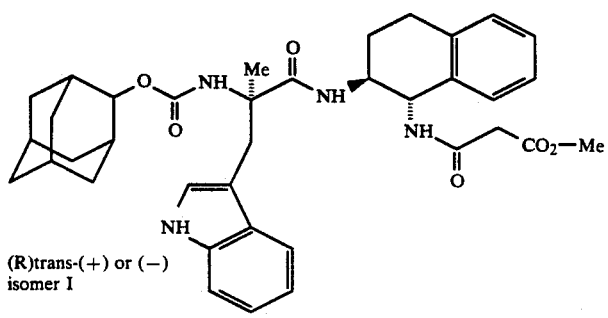

(R)trans-(+) or (−)
isomer I

-continued

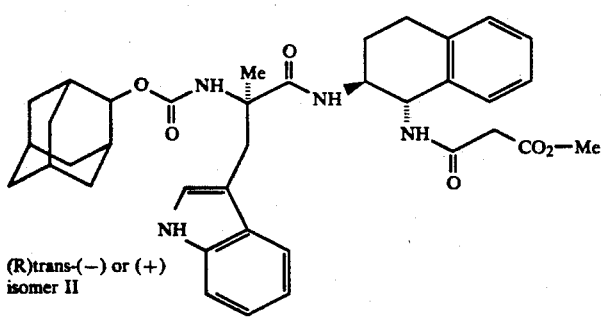

(R)trans-(−) or (+)
isomer II

A solution of the amine from Example 10, Step 2 (Scheme V, No. 6) (0.20 g, 0.4 mmol) in EtOAc (15 mL) was treated with methylmalonylchloride (0.06 g, 0.44 mmol) followed by triethylamine (0.03 g, 0.37 mmol) and stirred for 30 minutes at room temperature. This was then evaporated in vacuo and the residue separated by silica gel chromatography using 1:1 n-hexane:EtOAc as eluent to give two diastereoisomers separated as isomer I (0.05 g and Isomer II (0.06 g) (total yield 46%).

Isomer I: (Example 11, Propanoic acid, 3-[[2-[[3-(1H-indol-3-yl) -2-methyl-1-oxo-2-[[(tricyclo[3.3.1.1$^{3,7}$]dec-2-yloxy)carbonyl]amino]propyl]amino]-1,2,3,4-tetrahydro-1-naphthalenyl]amino]-3-oxo-, methyl ester), m.p. 140°–145° C.; $[\alpha]_D^{24} = +38.4°$ (c=0.25, MeOH); IR (film) 3500–3200, 2907, 2857, 1760–1700 (br), 1651, and 1491 cm$^{-1}$; NMR (CDCl$_3$) δ 1.50–2.15 (19H, m), 2.75–2.87 (1H, m), 2.90–3.05 (1H, m), 3.35 m), 4.82 (1H, s), 5.15 (1H, b, J 10 Hz), 5.34 (1H, s), 6.86 (1H, d, J 7.5 Hz), 7.00–7.35 (9H, m), 7.65 (1H, d, J 8 Hz), 8.17 (1H, s); MS m/e (FAB) 641 (10), 263 (10), 173 (39), and 135 (100). Analysis for C$_{37}$H$_{44}$N$_4$O$_6$: Calcd: C, 69.35; H, 6.92; N, 8.74. Found: C, 69.22; H, 6.86; N, 8.72.

EXAMPLE 12

Propanoic acid, 3-[2-[3-1H-indol-3-yl)-2-methyl-1-oxo-2-[[(tricyclo[3.3.1.3$^{,7}$]dec-2-yloxy)carbonyl]-amino]propyl]amino]-1,2,3,4-tetrahydro-1-naphthalenyl]amino]-3-oxo-, methyl ester, Isomer II M.p. 142°–183.5° C.; $[\alpha]_D^{244} = +26.8°$ (c=2.5, MeOH); IR (film) 3500–3200, 2910, 2854, 1760 1600 (br), 1651 and 1536 cm$^{-1}$; MR (CDCl$_3$) δ 1.45–2.05 (18H, m), 2.15–2.30 (1H, m), 2.80–2.90 (1H, m), 2.95–3.10 (1H, m), 3.24 (1H, d, J 17 Hz); 3.31 (1H, d, J 17 Hz), 3.39 (1H, d, J 15 Hz), 3.45 (1H, d, J 15 Hz), 3.73 (3H, s), 3.95–4.19 (1H, m), 4.81 (1H, s), 5.17 (1H, t, J 7 Hz, 5.23 (1H, s), 6.93 (1H, d, J 7 Hz), 6.97 (1H, d, J 2 Hz), 7.05–7.30 (6H, m), 7.34 (1H, d, J 8 Hz), 7.38 (1H, d, J 9 Hz), 7.60 (1H, d, J 8 Hz), 8.15 (1H, s); MS m/e (FAB) 641 (8), 263 (10), 173 (40), and 135 (100). Analysis for C$_{37}$H$_{44}$N$_4$O$_6$·0.25 H$_2$O: Calcd: C, 68.87; H, 6.95; N, 8.68. Found: C, 68.98; H, 7.08; N, 8.33.

Example 13 (Scheme VI, No. 11)

2-Butanoic acid, 1-[[1,2,3,4-tetrahydro-2-[[3 (1H-indol-3-yl)-2-methyl-1-oxo-2-[[(tricyclo[3.3.1.1$^{3,7}$]-dec-2-yloxy)carbonyl]amino]propyl]amino)-1-naphthalenyl]amino]-4-oxo-, methyl ester

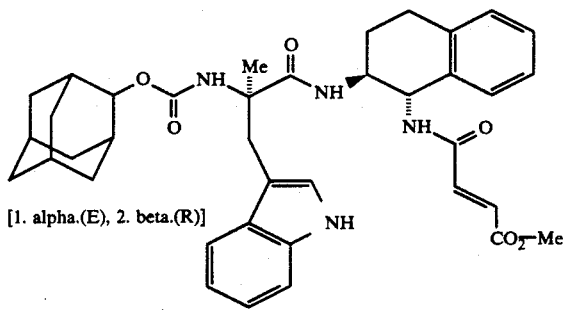

[1. alpha.(E), 2. beta.(R)]

A solution of the amine from Example 9, Step 2 (Scheme V, No. 6) (0.6 g, 1.1 mmol) in EtOAc (25 mL) was treated with methylpentafluorophenyl fumarate (0.5 g, 1.7 mmol) and the resultant mixture stirred 18 hours at room temperature. The solvent was then removed in vacuo and the residue chromatographed over silica gel using 3:1 EtOAc:hexane as eluent to give the product as a white, noncrystalline solid and a mixture of two diastereoisomers (0.35 g, 50%); m.p.=234°–236° C.; $[\alpha]_D^{20} = +10.4°$ (c=0.5, MeOH); IR (film) 3500–3200, 2912, 2854, 1715, 1646, and 1538 cm$^{-1}$; NMR (CDCl$_3$) δ 1.34 (1.5H, s), 1.45–2.20 (17.5H, m), 2.70–2.90 (2H, m), 3.16 (0.5H, d, J 14.5 Hz), 3.27 (0.5H, d, J 6.5 Hz), 3.32 (0.5H, d, J 7 Hz), 3.42 (0.5H, d, J 14.5 Hz), 3.72 (1.5H, s), 3.74 (1.5H, s), 3.90–4.10 (1H, m), 4.75–4.85 (1H, m), 5.10 5.30 (2H, m), 6.70–7.35 (12H, m), 7.53 (0.5H, d, J 8 Hz), 7.60 (0.5H, d, J 8 Hz), 8.31 (0.5H, s), 8.37 (0.5H, s). Analysis for C$_{38}$H$_{44}$N$_4$O$_6$·0.25-H$_2$O: Calcd: C, 69.44; H, 6.82; N, 8.52. Found: C, 69.55; H, 6.71; N, 8.49.

Example 14 (Scheme VIII, No. 20)

Butanoic acid, 4-oxo 4-[[1,2,3,4-tetrahydro-2-3-(1H-indol-3-yl)-2-methyl-1-oxo-2-[(tricyclo[3.3.1.1³,⁷]-dec-2-yloxy)carbonyl]amino]propyl]amino]-1-naphthalenyl]amino)-

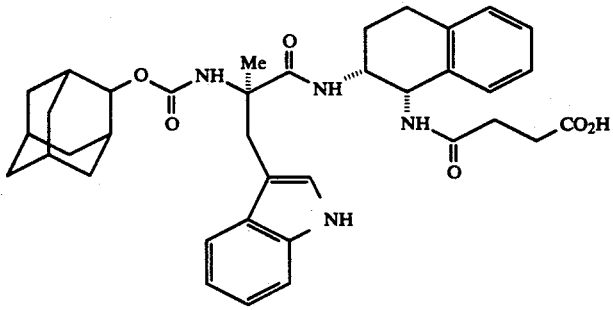

Step 1. Phenylmethyl (±)-trans-(1,2,3,4-tetrahydro-2-iodo-1-naphthalenyl)carbamate (Scheme VII, No. 13)

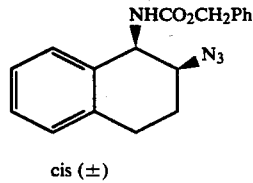

trans (±)

A solution of 1,2-dihydronaphthalene (10.0 g, 76.8 mmol) and iodine (19.5 g, 76.8 mmol) in anhydrous ether (200 mL) was treated with silver cyanate (17.27 g, 115.2 mmol) at 10° C. This mixture was stirred for 30 minutes, allowed to warm to room temperature, and left stirring a further 18 hours, then put under reflux for 1.5 hours. This suspension was then filtered, the filtrate evaporated to dryness in vacuo. Benzyl alcohol (100 mL) was then added and the reaction mixture stirred for 3 hours at room temperature. Excess benzyl alcohol was distilled off in vacuo and the residue crystallized and recrystallized from methanol to give the benzyl urethane (19.12 g, 61%) as a white solid; m.p. 141.2° C. (MeOH); IR (film) 3500–3200, 1697, and 1518 cm$^{-1}$; NMR (CDCl$_3$) δ 2.05–2.25 (2H, m), 2.75–2.85 (1H, m), 2.90–3.05 (1H, m), 4.55–4.70 (1H, br s), 5.05 5.25 (4H, m), 7.05–7.35 (9H, m). Analysis for C$_{18}$H$_{18}$INO$_2$: Calcd: C, 53.9; H, 4.45; N, 3.44. Found: C, 53.29; H, 4.42; N, 3.45.

Step 2. Phenylmethyl (±)-cis-(2-azido-1,2,3,4-tetrahydro-1-naphthalenyl)carbamate (Scheme VII, No. 14)

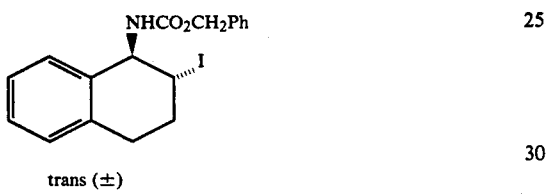

cis (±)

A solution of the benzyl urethane from Step 1 (Scheme VII, No. 13) (7.62 g, 18.7 mmol) in DMF (100 mL) was treated with sodium azide (1.46 g, 22.5 mmol) and the resulting mixture stirred 18 hours at room temperature. The solvent was then removed in vacuo and the residue suspended between H$_2$O and EtOAc. The organic phase was washed with saturated NaHCO$_3$ solution (2×20 mL), brine (2×20 mL), and H$_2$O (2×20 mL) and then dried over MgSO$_4$, filtered, and the solvent removed in vacuo. The residue was crystallized and recrystallized from MeOH to give the azide (2.94 g, 49%), m.p. 103.7° C. (MeOH); NMR (CDCl$_3$) 2.00–2.25 (2H, m), 2.70–2.85 (1H, m), 2.95–3.10 (1H, m), 4.05–4.20 (1H, br s), 5.00–5.25 (4H, m), 7.05–7.40 (9H, m); IR (film) 3500–3200, 2101, 1697, and

Step 3. Phenylmethyl (±)-cis-(2-amino-1,2,3,4-tetrahydro-1-naphthalenyl)carbamate (Scheme VII, No. 15)

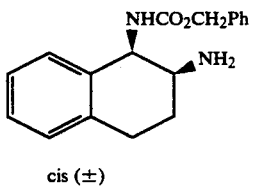

cis (±)

A solution of the azide from Step 2 (Scheme VII, No. 14) (2.00 g, 6.20 mmol) in absolute EtOH (150 μL) was treated with Lindlar catalyst (1.0 g, 50% w/w) and put under an atmosphere of hydrogen at a pressure of 50 psi for 2 hours at 25° C. This mixture was then filtered over gypsum and the filtrate evaporated to dryness in vacuo. The residue was separated by column chromatography over silica gel using 10% MeOH in CH$_2$Cl$_2$ as eluant to give the amine which was recrystallized from ether (1.3 g, 67%), m.p. 102°–145° C. (Et$_2$O); IR (film) 3500–3200, 1710, 1530, and 1454 cm$^{-1}$; NMR (CDCl$_3$) δ 1.70–1.95 (2H, m), 2.75 3.00 (2H, m), 3.15–3.25 (1H, m), 4.80 (3H, s), 4.91 (1H, d, J 4 Hz), 5.10 (1H, d, J 12.5 Hz), 5.16 (1H, d, J 12.5 Hz), 7.05–7.40 (9H, m). Analysis for C$_{18}$H$_{20}$N$_2$O$_2$: Calcd: C, 72.94; H, 6.80; N, 9.45. Found: C, 72.84; H, 6.81; N, 9.44.

Step 4. Carbamic acid, 1-(1H-indol 3-ylmethyl)-1-methyl-2-oxo-2-[[1,2,3,4-tetrahydro-1-[[phenyl-methoxy)carbonyl]amino]-2-naphthalenyl]amino]ethyl]-tricyclo[3.3.1.1³,⁷]dec-2-yl ester (Scheme VII, No. 16)

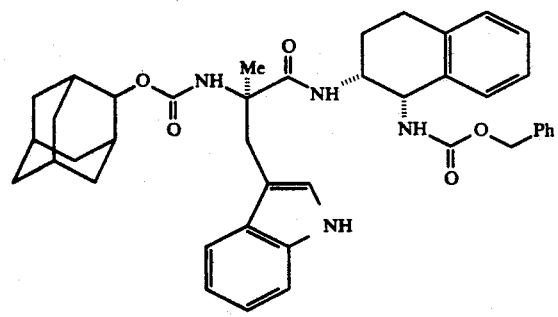

A solution of 2-adamantyloxycarbonyl-α-methyl-1-tryptophan (5.94 g, 15.1 mmol) and pentafluorophenol (2.78 g, 15.1 mmol) in EtOAc (150 mL) was treated at 0° C. with N,N'-dicyclohexylcarbodiimide (3.11 g, 15.1 mmol). This mixture was stirred for 2 hours at 0° C., filtered, and the amine prepared in Step 3 (Scheme III, No. 15) (5.17 g, 16.6 mmol) was added to the filtrate. This mixture was then stirred for 48 hours at room temperature before being washed with IM citric acid solution (2×20 mL), saturated NaHCO₃ solution (2×20 mL), and H₂O (2×20 mL). The organic phase was dried over MgSO₄, filtered, and the filtrate evaporated to dryness in vacuo. The residue was separated by chromatography over reverse phase silica gel using MeOH:H₂O (4:1) as eluant to give the product (7.21 g, 70%).

Step 5. Tricyclo[3.3.1.1³,⁷]dec-2yl[1R-[1α,2α(R*)]-]and 1S-[1α,2α(S*)]]-[2-[(1-amino-1,2,3,4-tetrahydro-2-naphthalenyl)amino]-1-(1H-indol-3-ylmethyl)-1-methyl-2-oxoethyl]carbamate (Scheme VII, No. 17)

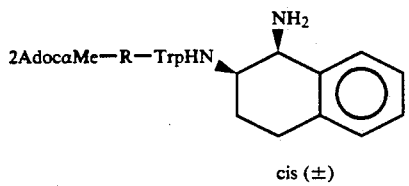

cis (±)

A solution of the benzyl urethane from Step 4 (Scheme VII, No. 16) (1.0 g, 1.5 mmol) in absolute EtOH (150 mL) was treated with 10% palladium on carbon (0.2 g, 20% w/w) and put under an atmosphere of hydrogen at a pressure of 50 psi at 25° C. for 4 hours. The mixture was then filtered over celite and the filtrate evaporated to dryness in vacuo to give the product (0.79 g, 100%), which is used immediately in the next step.

Step 6. [1R-[1α,2α(R*)] and [1S-[1α,2α(S*)]]-4-[[decahydro-2-]]3-(1H-indol-3-yl)-2-methyl-1-oxo-2-[[(tricyclo[3.3.1.1³,⁷]dec-2-yloxy)carbonyl]amino]-propyl]amino]-1-naphthalenyl]amino]-4-oxobutanoic acid (Scheme VIII, No. 20)

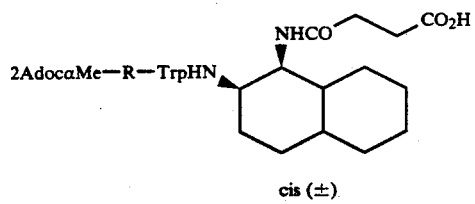

cis (±)

A solution of the amine prepared in Step 5 (Scheme VII, No. 17) (0.4 g, 0.73 mmol) in EtOAc (30 mL) was treated with succinic anhydride (0.09 g, 0.9 mmol) and the resulting solution stirred 18 hours at room temperature. The mixture was then washed with 1M HCl solution (20 mL), saturated NaHCO₃ solution (2×20 mL), and H₂O (2×20 mL). The organic phase was dried over MgSO₄, filtered, and the filtrate evaporated to dryness in vacuo. The residue was separated over reverse phase silica gel using MeOH:H₂O (3:1) as eluant to give the product as a noncrystalline white solid (0.27 g, 57%), m.p. 213°-238° C.; IR (film) 3500-3200, 2911, 2852, 1696, 1661, and 1515 cm⁻¹; NMR (DMSO-d₆, D2O) δ 1.27 (1.5H, s), 1.35 (1.5H, s), 1.36-1.50 (2H, m), 1.67-2.06 (14H, m), 2.17-2.40 (4H, m), 2.60-2.95 (2H, m), 3.12 (0.5H, d, J 14.5 Hz), 3.18-3.34 (1H, m), 3.39-3.55 (0.5H, m), 4.00-4.15 (1H, br s), 4.57-4.67 (1H, br s), 5.12 (0.5H, d, J 4.4 Hz), 5.15 (0.5H, d, J 4.4 Hz), 6.85-6.98 (1H, m), 6.97-7.24 (6H, m), 7.30 (0.5H, d, J 8 Hz), 7.31 (0.5H, d, J 8 Hz), 7.40 7.55 ( H, m).

Example 15 (Scheme VIII, No. 21)

Pentanoic acid, 5 oxo-5-[[1,2,3,4-tetrahydro-2-[3-(1H-indol-3-yl) -2-methyl-1-oxo-2-[[(tricyclo[3.3.1.13,7]dec-2-yloxy)-carbonyl]amino]propyl]amino]-1-naphthalenyl]amino]-[1S-[1α,2α(S*)]] and [1R-[1α,2α(R*)]]

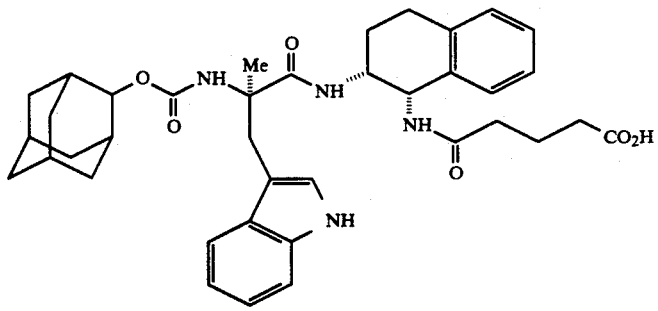

Method exactly as for Example 14 except using glutaric anhydride in Step 6 instead of succinic anhydride (yield 0.29 g, 60%), m.p. 196°-206° C.; IR 1515 cm⁻¹; NMR (DMSO-d₆, D2O) δ 1.27 (1.5H, s), 1.31 (1.5H, s), 1.37-1.53 (2H, m), 1.5-2.25 (20H, m), 2.60-2.95 (2H, m), 3.10 (0.5H, d, J 14.5 Hz), 3.28 (0.5H, d, J 16.3 Hz), 3.37 (0.5H, d, J 16.3 Hz), 3.39 4.50 (0.5H, m), 3.97-4.18 (1H, br s), 4.53-4.66 (1H, br s), 5.13 (0.5H, d, J 4 Hz), 5.17-5.23 (0.5H, br s), 6.83-7.24 (7H, m), 7.31 (1H, d, J 7.3 Hz), 7.44 (0.5H, d, J 8.5 Hz), 7.46 (0.5H, d, J 8 Hz).

Example 16 (Scheme VIII, No. 18)

Propanoic acid,
3-oxo-3-[[1,2,3,4-tetrahydro-2-[[3-(1H-indol-3-yl)
-2-methyl-1
oxo-2-[[(tricyclo-[3.3.1.1³,⁷]dec-2-yloxy)carbonyl-
]amino]propyl]amino]-1-naphthalenyl]amino]-,methyl
ester

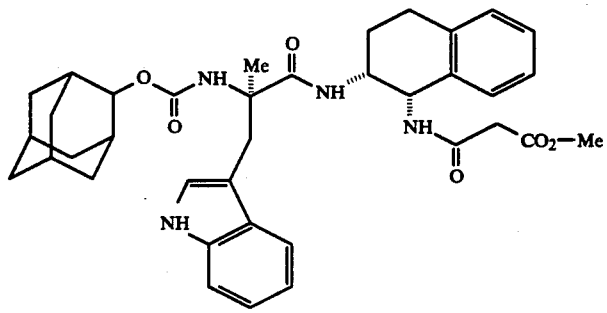

A solution of the amine as prepared in Example 14, Step 5 (Scheme VII, No. 17) (0.8 g, 1.5 mmol) and methyl malonyl chloride (0.24 g, 1.77 mmol) in EtOAc (60 mL) was treated with triethylamine (0.15 g, mmol) and the resulting mixture stirred 18 hours at room temperature. This mixture was then washed with 1 M citric acid solution (3×20 mL), saturated NaHCO$_3$ solution (2×20 mL), and H$_2$O (2×20 mL). The organic phase was dried over MgSO$_4$, filtered, and filtrate evaporated in vacuo to dryness. The residue was then purified by reverse phase silica gel chromatography using MeOH:-H$_2$O (3:1) as eluant to give the product, m.p. 130.7°–154.9° C.

Example 17 (Scheme VIII, No. 22)

2-Butenoic acid, 4-oxo
4-[[1,2,3,4-tetrahydro-2-[3-(1H-indol-3-yl)
-2-methyl-1-oxo-2-[[(tricyclo[3.3.1.1³
⁷]dec-2-yloxy)carbonyl]amino]propyl]amino]-1-naph-
thalenyl]amino]-, methyl ester

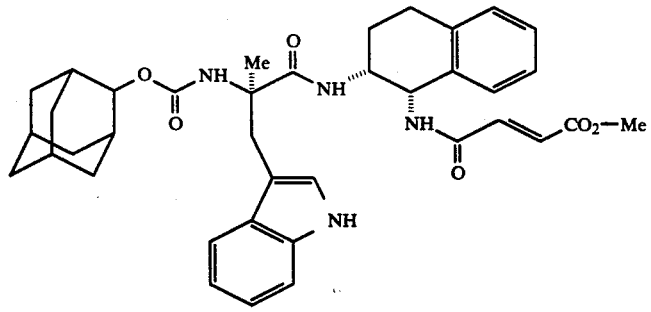

A solution of the amine as prepared in Example 14, Step 5 (Scheme VII, No. 17) (0.8 g, 1.5 mmol) in EtOAc (60 mL) was treated with methyl(pentafluorophenyl)-fumarate (0.65 g, 2.22 mmol) and stirred for 12 hours at room temperature. The mixture was evaporated to dryness in vacuo and the residue separated by reverse phase silica gel chromatography using MeOH:H$_2$O (3:1) as eluant to give the product (0.52 g, 56%), m.p. 142.6°–146.1° C.

We claim:
1. A compound of formula

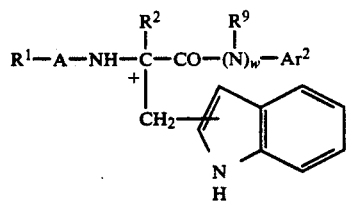

or a pharmaceutically acceptable salt thereof wherein:
R$^1$ is a

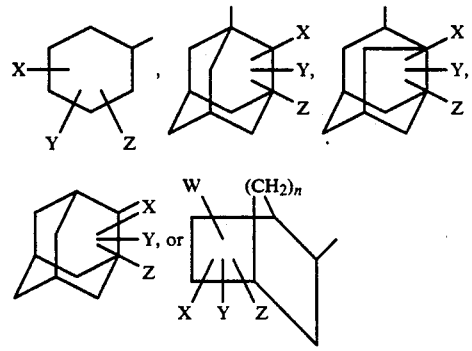

where W, X, Y, and Z are each independently hydrogen, a straight or branched alkyl of from one to six carbon atoms CF$_3$, NR$^5$R$^6$, —(CH$_2$)$_n$CO$_2$R*, or CN, F, Cl, Br, OR*, SR*, wherein R* is hydrogen or a straight or branched alkyl of from one to six carbon atoms and wherein R$^5$ and R$^6$ are each independently hydrogen or alkyl of from one to six carbon atoms and n is an integer of from one to three;

A is —(CH$_2$)$_n$CO—, —SO$_2$—, —SO—, —NHCO—,

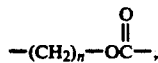

—SCO—, —O—(CH$_2$)$_n$CO— or —HC=CH-CO— wherein n is an integer from zero to six;

R$^2$ is a straight or branched alkyl of from one to six carbon atoms, —HC=CH$_2$, —C≡CH, —(CH$_2$)$_n$—CH=CH$_2$, —(CH$_2$)$_n$C≡CH, —(CH$_2$)$_n$OR*, —(CH$_2$)—(CH$_2$)$_n$CO$_2$R*, —(CH$_2$)$_n$NR$^5$R$^6$ wherein n, R*, R$^5$, and R$^6$ are as defined above;

R$^9$ is H, or a straight or branched alkyl of from one to six carbon atoms, —(CH$_2$)$_n$CO$_2$R*, (CH$_2$)$_n$NR$^5$R$^6$, wherein n, R*, R$^5$, and R$^6$ are as defined above and w is 1;

Ar$^2$ is

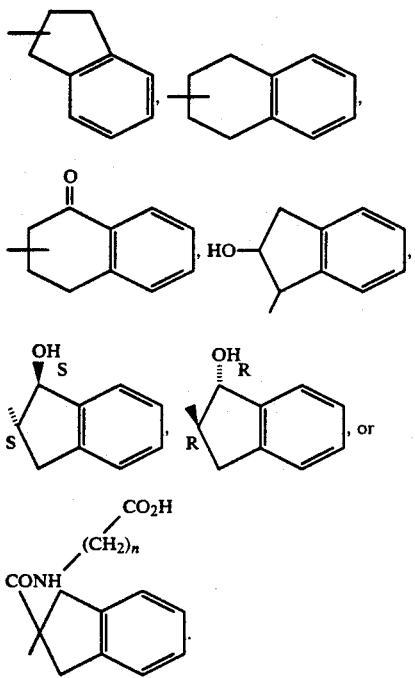

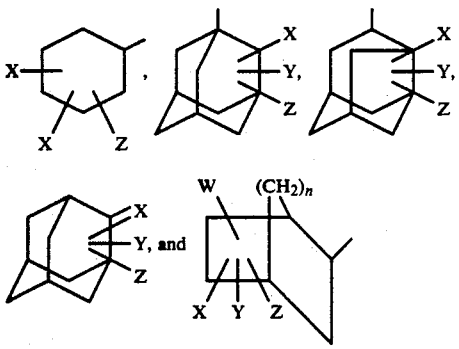

2. A compound according to claim 1 wherein R$^1$ is

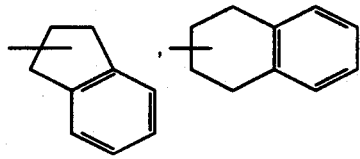

where W, X, Y, and Z are each independently hydrogen, a straight or branched alkyl of from one to six carbon atoms CF$_3$, NR$^5$R$^6$, —(CH$_2$)$_n$CO$_2$R*, or CN, F, Cl, Br, OR*, SR*, wherein R* is hydrogen or a straight or branched alkyl of from one to six carbon atoms and wherein R$^5$ and R$^6$ are each independently hydrogen or alkyl of from one to six carbon atoms and n is an integer of from 1 to 3;

A is —NHCO—,
—OCO—,
—SO$_2$—,
—S(=O)—,
—CH$_2$CO—,

R$^2$ is —CH$_3$,
—CH$_2$CO$_2$CH$_3$,
—CH$_2$C≡CH,

R$^9$ is hydrogen, when w is 1, Ar$^2$ is unsubstituted or substituted in the manner indicated above, and Ar$^2$ can also be:

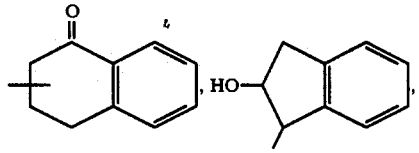

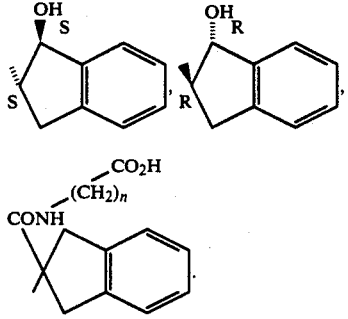

3. A compound according to claim 2 wherein:
R$^1$ is 2-adamantyl or 1-(S)-2-endobornyl,
A is

R$^2$ is —CH$_3$,

Ar$^2$ is unsubstituted or substituted by one to three substitutents each independently selected from hydrogen, —CH$_2$OH, —CH$_2$OCOCH$_2$CH$_2$COOH, —CH$_2$OCOCH=CHCO$_2$H, —CH$_2$NHCOCH$_2$CH$_2$COOH, —CH$_2$NHCOCH=CHCO$_2$H, —NHCOCH$_2$CH$_2$CO$_2$H, —NHCOCH=CHCO$_2$H, —NHCOCH2CH2CO$_2$H, —NHCOCHαCHCO$_2$H, oxo, hydroxy, phenyl, CO$_2$Me, CONHCH$_2$CH$_2$CO$_2$Bz, —CO$_2$Bz, —CONHCH$_2$CO$_2$H, —CONHCH$_2$CH2CO$_2$H, —SCH$_2$CO$_2$H, —SCH$_2$CH$_2$CO$_2$H.

4. A compound according to claim 1 selected from carbamic acid, [2-[(2,3-dihydro-2-hydroxy-1H-inden-1-yl)amino]-1-(1H-indol-3-ylmethyl)-1-methyl-2-oxoethyl]-, 1,7,7-trimethylbicyclo-[2.2.1]hept-2-yl ester (bicyclo ring is 1S-endo (+-isomer), trp center is D, indene ring centers are unknown), carbamic acid, [2-[(2,3-dihydro-1-hydroxy-1H-inden-2-yl)amino]-1-1H-indol-3 ylmethyl)-2-methyl-2-oxoethyl]-, 1,7,7-trimethylbicyclo-[2.2.1]hept-2-yl ester, [1S*[1α,2β[S-(trans)],4β]]- (Bicyclo system is 1S-endo), and carbamic acid, [2-[(2,3-dihydro-1 hydroxy-1H-inden-2-yl)amino]-1-(1H-indol-3-ylmethyl)-1-methyl-2-oxoethyl]-, 1,7,7-trimethylbicyclo-[2.2.1]hept-2-yl ester, [1S-[1α,2β[S*(1S*,2S*)],4α]]- [Bicyclo system is 1S-endo, all other centers are R].

5. A compound according to claim 1 selected from
carbamic acid, [1-(1H-indol-3-ylmethyl)-1-methyl-2-oxo-2-[(1,2,3,4-tetrahydro-1-oxo-2-naphthalenyl)amino]ethyl]-, 1,7,7-trimethyl-bicyclo[2.2.1]hept-2-yl ester (Bicyclo system 1S-endo; TRO center R; naphthyl center (−) or (+)), (Isomer II) and
carbamic acid, [1-(1H-indol-3-ylmethyl)-1-methyl-2-oxo-2-[(1-2,3,4-tetrahydro-1-oxo-2-naphthalenyl)amino]ethyl]-, 1,7,7-trimethylbicyclo[2.2.1]hept-2-yl ester (Bicyclo system 1S-endo; TRP center R; naphthyl center (+) or (−)), (Isomer I).

6. A compound according to claim 1 selected from
carbamic acid, [1-(1H-indol-3-ylmethyl)-1-methyl-2-oxo-2-[(1,2,3,4-tetrahydro-1-naphthalenyl)amino]ethyl]-, tricyclo[3.3..1.1$^{3,7}$]-dec-2-yl ester, (±)- and
carbamic acid, [1-1H-indol-3-ylmethyl)-1-methyl-2-oxo-2-[(1,2,3,4-tetrahydro-2-naphthalenyl)amino]ethyl]-, tricyclo[3.3.1.1$^{3,7}$]-dec-2-yl ester, (±)-.

7. A compound according to claim 1 named 4-[[1,2,3,4-tetrahydro-2-[[3-(1H-indol-3-yl)-2-methyl-1-oxo-2-[[(tricyclo[3.3.1.1$^{3,7}$]dec-2-yloxy)carbonyl]amino]propyl]amino]-1-naphthalenyl]amino]-4-oxobutanoate.

8. A compound according to claim 1 named tricyclo[3.3.1.1$^{3,7}$]dec-2-yl-[2-[(1-azido-1,2,3,4-tetrahydro-2-naphthalenyl)amino]-1(1H-indol-3-ylmethyl)-1-methyl 2-oxoethyl]carbamate.

9. A compound according to claim 1 named methyl 3-[[2-[[3 (1H-indol-3-yl)-2 methyl-1-oxo-2-[[(tricyclo[3.3.1.1$^{3,7}$]dec 2-yloxy)carbonyl]amino]propyl]amino]-1,2,3,4-tetrahydro-1-naphthalenyl]amino]-3-oxopropanoate.

10. A compound according to claim 1 named methyl 3-[[2-[[3-(1H-indol-3-yl)-2-methyl-1-oxo-2-[[(tricyclo[3,3,1,1$^{3,7}$]dec-2-yloxy)carbonyl]amino]propyl]amino]-1,2,3,4-tetrahydro-1-naphthalenyl]amino]-3-oxopropanoate.

11. A compound according to claim 1 named methyl 1-[[1,2,3,4-tetrahydro-2-[[3-(1H-indol-3-yl)-2-methyl-1-oxo-2-[[(tricyclo[3.3.1.1$^{3,7}$]dec-2-yloxy)carbonyl]amino]propyl]amino]-1-naphthalenyl]amino]-4-oxo-2-butanoate.

12. A pharmaceutical composition comprising an amount of a compound according to claim 1, effective to reduce anxiety in a mammal, and a pharmaceutically acceptable carrier.

* * * * *

UNITED STATES PATENT AND TRADEMARK OFFICE
CERTIFICATE OF CORRECTION

PATENT NO. : 5,244,915
DATED : Sept. 14, 1993
INVENTOR(S) : Horwell, et al

It is certified that error appears in the above-indentified patent and that said Letters Patent is hereby corrected as shown below:

On title page, item [54] and col. 1, line 1, "AMICO" should read "AMINO".

Column 49, line 9, delete the first "≡" and insert instead "=".

Column 49, line 10, delete the first "-($CH_2$)".

Column 50, line 58, all "2's" in the line should be subscripts.

Column 50, line 59, delete "α" and insert instead "=".

Column 51, line 2, a "-" should be inserted after the "3".

Column 51, line 6, a "-" should be inserted after the first "1".

Column 51, line 15, "TRO" should be "TRP".

Column 52, line 10, a "-" should be inserted after the first "3" and after the second "2".

Column 52, line 11, insert a "-" after "dec".

UNITED STATES PATENT AND TRADEMARK OFFICE
CERTIFICATE OF CORRECTION

PATENT NO. : 5,244,915

DATED : Sept. 14, 1993

INVENTOR(S) : Horwell, et al

It is certified that error appears in the above-indentified patent and that said Letters Patent is hereby corrected as shown below:

Column 52, line 16, delete "," three times and insert instead "." three times.

Signed and Sealed this

Twelfth Day of April, 1994

Attest:

BRUCE LEHMAN

Attesting Officer     Commissioner of Patents and Trademarks